(12) United States Patent
Pozzi et al.

(10) Patent No.: US 12,060,396 B2
(45) Date of Patent: Aug. 13, 2024

(54) FUSED IN SARCOMA (FUS) NUCLEAR TRANSLOCATION INHIBITORS FOR PREVENTING FIBROSIS

(71) Applicants: Vanderbilt University, Nashville, TN (US); The United States as Represented by The Department of Veterans Affairs, Washington, DC (US)

(72) Inventors: Ambra A. Pozzi, Nashville, TN (US); Manuel Chiusa, Nashville, TN (US); Jack J. Hawiger, Nashville, TN (US); Jozef Zienkiewicz, Nashville, TN (US)

(73) Assignees: Vanderbilt University, Nashville, TN (US); The United States as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/481,128

(22) PCT Filed: Jan. 29, 2018

(86) PCT No.: PCT/US2018/015702
§ 371 (c)(1),
(2) Date: Jul. 26, 2019

(87) PCT Pub. No.: WO2018/140863
PCT Pub. Date: Aug. 2, 2018

(65) Prior Publication Data
US 2019/0352355 A1    Nov. 21, 2019
US 2021/0332093 A9    Oct. 28, 2021

Related U.S. Application Data

(60) Continuation of application No. 15/297,996, filed on Oct. 19, 2016, now Pat. No. 10,568,928, which is a division of application No. 14/251,135, filed on Apr. 11, 2014, now Pat. No. 9,492,544.

(60) Provisional application No. 61/810,939, filed on Apr. 11, 2013.

(51) Int. Cl.
| | |
|---|---|
| *C07K 14/47* | (2006.01) |
| *A61K 38/17* | (2006.01) |
| *A61K 38/18* | (2006.01) |
| *A61K 45/06* | (2006.01) |
| *A61P 13/12* | (2006.01) |
| *C07K 14/50* | (2006.01) |
| *C07K 14/705* | (2006.01) |

(52) U.S. Cl.
CPC ...... *C07K 14/4703* (2013.01); *A61K 38/1709* (2013.01); *A61K 38/1777* (2013.01); *A61K 38/1825* (2013.01); *A61K 45/06* (2013.01); *A61P 13/12* (2018.01); *C07K 14/50* (2013.01); *C07K 14/70557* (2013.01); *C07K 2319/02* (2013.01); *C07K 2319/10* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,579,250 A | 11/1996 | Balaji et al. | |
| 5,612,895 A | 3/1997 | Balaji et al. | |
| 5,631,280 A | 5/1997 | Ciccarone et al. | |
| 5,925,565 A | 7/1999 | Berlioz et al. | |
| 5,935,819 A | 8/1999 | Eichner et al. | |
| 8,932,559 B2 | 1/2015 | Hawiger et al. | |
| 9,044,433 B2 | 6/2015 | Hawiger et al. | |
| 9,492,544 B2 * | 11/2016 | Hawiger | A61K 38/12 |
| 2008/0015137 A1 | 1/2008 | Chook | |
| 2010/0210534 A1 | 8/2010 | Bevec | |
| 2014/0309159 A1 | 10/2014 | Hawiger et al. | |

(Continued)

FOREIGN PATENT DOCUMENTS

| | | |
|---|---|---|
| WO | 1998/16241 | 4/1998 |
| WO | 1999047690 | 11/1999 |
| WO | 2015067712 | 5/2015 |

OTHER PUBLICATIONS

Niu C, Zhang J, Gao F, Yang L, Jia M, et al. (2012) FUS-NLS/Transportin 1 Complex Structure Provides Insights into the Nuclear Targeting Mechanism of FUS and the Implications in ALS. PLoS ONE 7(10): e47056. doi: 10.1371/journal.pone.0047056.*

(Continued)

*Primary Examiner* — Marianne P Allen
(74) *Attorney, Agent, or Firm* — Meunier Carlin & Curfman LLC

(57) ABSTRACT

Disclosed herein are compositions and methods for inhibiting collagen production mediated by the Fused in Sarcoma (FUS) ribonucleoprotein. As disclosed herein, the C terminal domain of FUS contains an uncommon nuclear localization sequence (NLS) motif called PY-NLS that binds the nuclear import receptor transportin. Phosphorylation of FUS leads to its association with transportin and nuclear translocation with consequent increased in collagen production. Therefore, disclosed herein is an isolated peptide having a transportin-binding moiety, which inhibits FUS from binding transportin, linked to a membrane translocating motif. These compositions and methods can be used to inhibit FUS-mediated collagen production, and treat fibrotic disease involving FUS-mediated collagen accumulation in kidneys and other organs displaying fibrotic diseases.

4 Claims, 25 Drawing Sheets
Specification includes a Sequence Listing.

(56) References Cited

U.S. PATENT DOCUMENTS

| | | |
|---|---|---|
| 2015/0191522 A1 | 7/2015 | Hawiger et al. |
| 2016/0177389 A1 | 6/2016 | Kwiatkowski, Jr. et al. |
| 2017/0226507 A1 | 8/2017 | Chan et al. |

OTHER PUBLICATIONS

Dormann et al., The EMBO Journal (2010) 29, 2841-2857.*
Axe et al., Journal of Molecular Biology, 301(3):585-595, 2000.*
Chichili et al., Protein Science, 22:153-167, 2013.*
International Search Report and Written Opinion dated Apr. 24, 2018, from International Application No. PCT/US2018/015702, 12 pages.
Zhang et al. "Structural and energetic basis of ALS-causing mutations in the atypical proline-tyrosine nuclear localization signal of the Fused in Sarcoma protein (FUS)", Proc Natl Acad Sci USA, Jul. 9, 2012, vol. 109, pp. 12017-12021.
Brooke et al. "FUS/TLS in a novel mediator of androgen-dependent cell-cycle progression and prostate cancer growth", Cancer Research, Dec. 17, 2011, vol. 71, pp. 914-924.
Niu et al. "FUS-NLS/Transportin 1 complex structure provides insights into the nuclear targeting mechanism of FUS and the implications in ALS", PLoS One, Oct. 8, 2012, vol. 7, No. 10, pp. 1-10.
Twyffels et al. "Transportin-1 and Transportin-2: protein nuclear import and beyond", FEBS Letters, Apr. 26, 2014, vol. 588, pp. 1857-1868.
Borza, C.M., et al. 2015. Curr Top Membr 76:231-253.
Ray K. Nat Rev Rheumatol 2013, 11:637.
Veach, R.A., et al. 2004. J Biol Chem 279:11425-11431.
Gardner, H., et al. 1996. Dev Biol 175:301-313.
Korbelin et al. Mol. Therapy,24(6):1050-1061 (2016).
Rosowski et al. Microb Cell Fact. Jan. 9, 2018;17(1):3.
Kelly, R.L. et al. J.Mol.Biol. 430(1):119-130 (2018).
Ghattas, I. R. et al., Mol. Cell. Biol., 11:5848-5849 (1991).
Macejak and Sarnow, Nature, 353:91 (1991).
Oh et al., Genes & Development, 6:1643-1653 (1992).
Pelletier and Sonenberg, Nature, 334:320-325 (1988).
Mountford and Smith, TIG, 11:179-184 (1985).
Hynes, R. 2002. Cell 110:673-687; Pan, L., et al. 2016. Springerplus 5:1094.
Patey, N., et al. 1994. Cell Adhes Commun 2:159-167.
Chen, X., et al. 2007. Mol Cell Biol 27:3313-3326.
Chen, X., et al. 2004. Am J Pathol 165:617-630.
Chen, X., et al. 2010. Mol Cell Biol 30:3048-3058.
Wang, H., et al. 2015. Kidney Int 87:948-962.
Gardner, H., et al. 1999. J Cell Sci 112:263-272.
Borza, C.M., et al. 2010. J Biol Chem 285:40114-40124.
Chen, X., et al. 2014. J Clin Invest 124:3295-3310.
Mattila, E., et al. 2005. Nat Cell Biol 7:78-85.
Borza, C.M., et al. 2012. J Am Soc Nephrol 23:1027-1038.
Zent, R., et al. 2006. Kidney Int 70:460-470.
Yu, L., et al. 2012. Kidney Int 81:1086-1097.
Rebelo, S., et al. 2015. Cell Signal 27:2589-2598; Thapar, R. 2015. ACS Chem Biol 10:652-666.
Zhuang, S., et al. 2014. Kidney Int Suppl (2011) 4:70-74.
Liu, N., et al. 2012. PLoS ONE 7:e36194.
Bollee, G., et al. 2011. Nat Med 17:1242-1250.
Zeng, F., et al. 2016. Am J Physiol Renal Physiol:ajprenal 311(4):F695-F707.
Abulrob, A., et al. 2004. Oncogene 23:6967-6979.
Luetteke, N.C., et al. 1994. Genes Dev 8:399-413.
Liu, F., et al. "Role of Receptor Tyrosine Kinase Signaling in Renal Fibrosis", Int J Mol Sci 17, 2016.
Sama, R.R., et al. 2014. ASN Neuro 6.
Dormann, D., et al. 2010. Embo J 29:2841-2857.
Kwiatkowski, T.J., Jr., et al. 2009. Science 323:1205-1208; Vance, C., et al. 2009. Science 323:1208-1211.
Sabatelli, M., et al. 2013. Hum Mol Genet 22:4748-4755.
Picher-Martel, V., et al. 2016. Acta Neuropathol Commun 4:70.
Sephton, C.F., et al. 2014. Proc Natl Acad Sci U S A 111:E4769-4778.
Hicks, G.G., et al. 2000. Nat Genet 24:175-179.
Thapar, R. 2015. ACS Chem Biol 10:652-666.
Shimamura, M., et al. 2014. Exp Cell Res 326:36-45.
Dhar, S.K., et al. 2014. Antioxid Redox Signal 20:1550-1566.
Ghosh, A.K., et al. 2013. Exp Biol Med (Maywood) 238:461-481.
Burbelo, P.D., et al. 1988. Proc Natl Acad Sci U S A 85:9679-9682.
Extended EP Search Report dated Oct. 12, 2020, from related EP Application No. 18744420, 7 pages.
Wynn, T.A. et al. "Mechanisms of fibrosis: therapeutic translation for fibrotic disease", Nature Medicine, vol. 18, No. 7, Jul. 2012, 13 pages.

* cited by examiner

FUSED IN SARCOMA (FUS) NUCLEAR TRANSLOCATION INHIBITORS FOR PREVENTING FIBROSIS

CROSS REFERENCE TO RELATED APPLICATION

This application is a national stage application filed under 35 U.S.C. § 371 of International Application No. PCT/US2018/015702, filed on Jan. 29, 2018 which claims the benefit of U.S. Provisional Patent Application Serial No. 62/451,636 filed Jan. 27, 2017, applications which are fully incorporated herein by reference in their entirety.

STATEMENT REGARDING FEDERALLY SPONSORED RESEARCH OR DEVELOPMENT

This invention was made with Government Support under Grant No. DK095761 awarded by the National Institutes of Health and Grant No. BX002025 from the Department of Veterans Affairs. The Government has certain rights in the invention.

The sequence listing submitted on Apr. 6, 2023, as an .txt file entitled "10644_034US1_ST25.XML" created on Feb. 11, 2022, and having a file size of 5292 bytes is hereby incorporated by reference pursuant to 37 C.F.R. § 1.52(e)(5).

BACKGROUND

End stage glomerular disease is the most common cause of chronic kidney failure and represents a major cause of morbidity and mortality for Veterans and civilian patients. Despite the fact that glomerular disease has multiple etiologies, the final pathology is characterized by overproduction and deposition of extracellular matrix (ECM) and ensuing glomerulosclerosis (Borza, C. M., et al. 2015. Curr Top Membr 76:231-253). In glomerulosclerosis, the synthesis and remodeling of ECM components (mainly collagens) are uncontrolled thus leading to scarred glomeruli characterized by abnormal collagen deposition, particularly collagens type I, IV, V and VI. Although many pathways have been implicated in both initiation and progression to glomerular fibrosis, to date there are very few therapeutic options to treat glomerulosclerosis. Thus, there is the need of identifying key factors contributing to the initiation and/or progression to glomerulosclerosis, and fibrotic diseases in other organs (e.g. liver, lungs, skin, retroperitoneal space), with the expectation that targeting such factors will help in slowing and ideally suppressing fibrotic responses, and ultimately reducing end stage kidney disease as well as other organs' fibrotic diseases.

SUMMARY

Disclosed herein are compositions and methods for inhibiting collagen production mediated by the Fused in Sarcoma (FUS) ribonucleoprotein. These compositions and methods can therefore be used to treat and prevent fibrotic disease in a subject, such as a subject with liver, kidney, or lung disease or damage.

As disclosed herein, the C terminal domain of FUS contains an uncommon nuclear localization sequence (NLS) motif called PY-NLS that binds the nuclear import receptor transportin. Phosphorylation of FUS leads to its association with transportin and nuclear translocation with consequent increased in collagen production. Therefore, disclosed herein is an isolated peptide that comprises a transportin-binding moiety, which inhibits FUS from binding transportin, linked to a membrane translocating motif.

In some embodiments, the transportin-binding moiety comprises a C-terminal fragment of a FUS ribonucleoprotein. For example, the transportin-binding moiety can comprise the amino acid sequence SRGEHRQDRRERPY (SEQ ID NO:1), or a conservative variant thereof.

In some embodiments, the membrane translocating motif comprises a signal sequence hydrophobic region (SSHR). For example, the SSHR can be derived from an integrin $\beta_3$ protein, such as a human integrin $\beta_3$ protein, or from a fibroblast growth factor 4 (FGF4) protein, such as a human FGF4 protein. In some embodiments, the membrane translocating motif comprises the amino acid sequence XXXXLLPXXLLALLAP (SEQ ID NO:2) or XXXXLLPXXLLAVLAP (SEQ ID NO:3), wherein X is any naturally occurring amino acid. In some embodiments, the membrane translocating motif comprises the amino acid sequence AAVALLPAVLLALLAP (SEQ ID NO:4) or AAVALLPAVLLAVLAP (SEQ ID NO:5).

In some embodiments, the polypeptide comprises the amino acid sequence AAVALLPAVLLALLAP (SEQ ID NO: 4)-SRGEHRQDRRERPY (SEQ ID NO: 1) or AAVALLPAVLLAVLAP (SEQ ID NO: 5)-SRGEHRQDR-RERPY (SEQ ID NO: 1), wherein "—" is a linker or peptide bond. Linkers can be short peptide sequences that occur between protein domains. The linkers can be flexible or rigid. Flexible linkers are often composed of flexible residues like glycine and serine so that the adjacent protein domains are free to move relative to one another. In particular, the linker can be a polyglycine (e.g. 3, 4, or 5 glycine), a polyserine (e.g. 3, 4, or 5 serine), or a combination of glycine and serine including repeating combinations. For example, the linker can be a glycine and serine linker, such as, for example, a G4S, GSG4, G2SG3SG2, G2SG, G3S linker, or any other linker known in the art where the base linker sequence can optionally be repeated 2, 3, 4, or more times. In some embodiments, the polypeptide comprises the amino acid sequence (SEQ ID NO: 8)
AAVALLPAVLLALLAPSRGEHRQDRRERPY or (SEQ ID NO: 9)
AAVALLPAVLLAVLAPSRGEHRQDRRERPY.

The disclosed peptide can further include one or more additional moieties. For example, the peptide can contain a homing peptide or organ-specific or cell-specific Fab antibody fragment for targeted delivery to an organ, such as the lung, kidney, skin, heart, pancreas, uterus, retina, intestines, prostate, or liver. The peptide can also contain a label, such as a fluorescent dye.

Also disclosed is a method for decreasing FUS-mediated collagen production by a cell, comprising contacting the cell with an effective amount of a composition comprising an agent that inhibits nuclear translocation of FUS. Also disclosed is a method for treating fibrotic disease in a subject that involves administering to the subject a therapeutically effective amount of a composition comprising an agent that inhibits nuclear translocation of FUS.

In some embodiments, the agent used in the disclosed methods inhibits FUS from binding transportin. For example, the agent can compete with FUS for binding to transportin, or can compete with transportin for binding to FUS. In some embodiments, the agent comprises a peptide disclosed herein having a transportin-binding moiety linked to a membrane translocating motif.

The disclosed method can be used to treat any condition involving abnormal FUS-mediated collagen formation. In particular, the method can be used to treat a fibrosis involving abnormally excessive collagen accumulation. For example, the subject can have a kidney disease or damage, wherein the method inhibits glomerulosclerosis in the subject. The subject can have a liver disease or damage, wherein the method inhibits cirrhosis in the subject. The subject can have a lung disease or damage, wherein the method inhibits pulmonary fibrosis in the subject. The subject can have a retroperitoneal fibrosis, wherein the method inhibits the formation of fibrous tissue in the retroperitoneum. The subject can have skin fibrosis (scleroderma) associated with systemic sclerosis in which integrins and transforming growth factor beta as well as connective tissue growth factor play significant role (Ray K. Nat Rev Rheumatol 2013, 11:637

The subject can have a fibrosarcoma or osteosarcoma tumor, wherein the method inhibits collagen production by the tumor.

The disclosed compositions can further contain or be administered with other diagnostic or therapeutic agents for fibrosis. For example, the disclosed composition can contain or be administered with a corticosteroid or a non-steroidal anti-inflammatory agent. In some embodiments, the disclosed composition contains or is administered with a nuclear transport modifier (NTM) that targets nuclear transport by an importin, such as those described in U.S. Pat. Nos. 8,932,559, 9,044,433, and 9,492,544, which are incorporated by reference in their entirety for the teaching of these NTM molecules and uses thereof.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
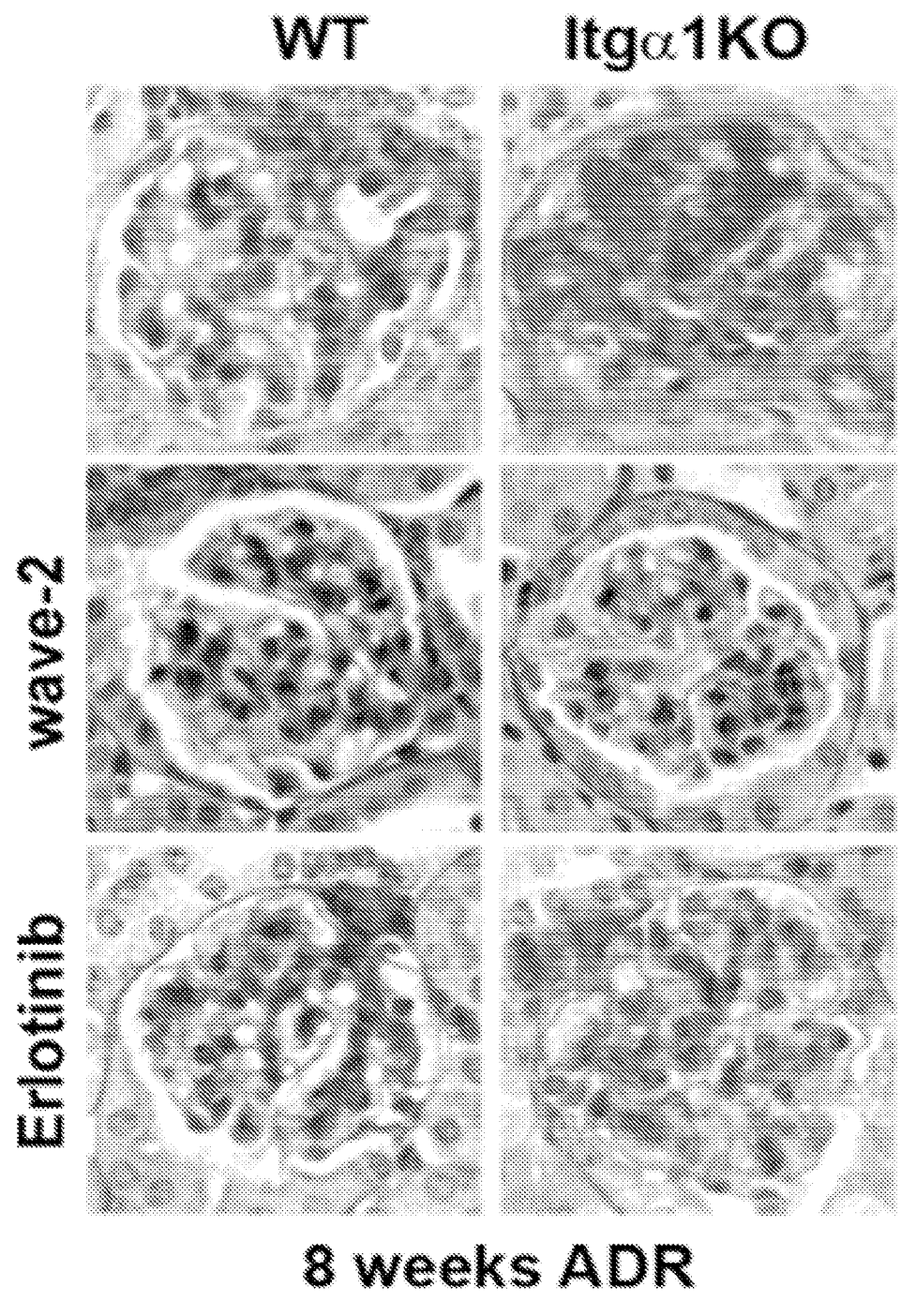
FIGS. 1A to 1E. (A) Images of glomeruli from BALB/c WT and Itgα1KO mice 8 weeks after ADR injection. Note that crossing the Itgα1KO mice with the wave-2 mice or treating them with erlotinib improved glomerular injury (A), albuminuria (mean±SEM of 5-7 mice/group) (B, C), and kidney collagen IV levels (erlotinib group shown only, mean±SEM of 3 mice/group) (D, E).
Figure 1B:
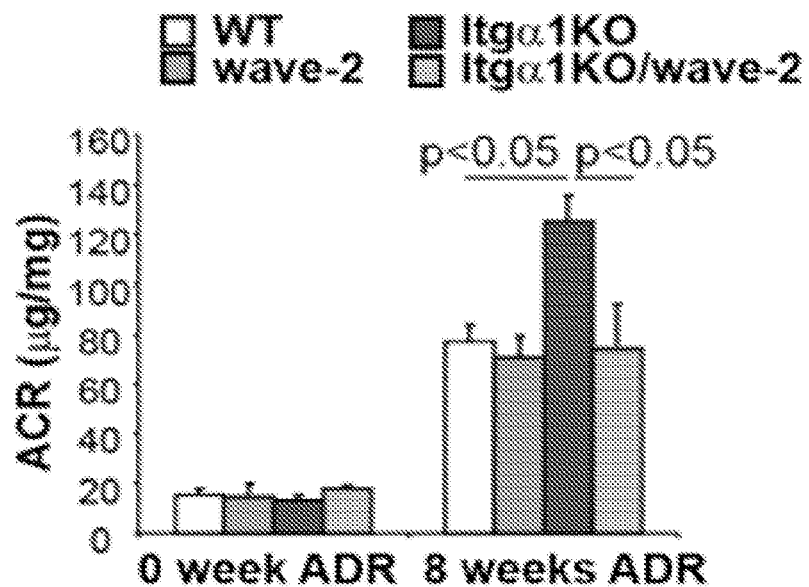
Figure 1C:
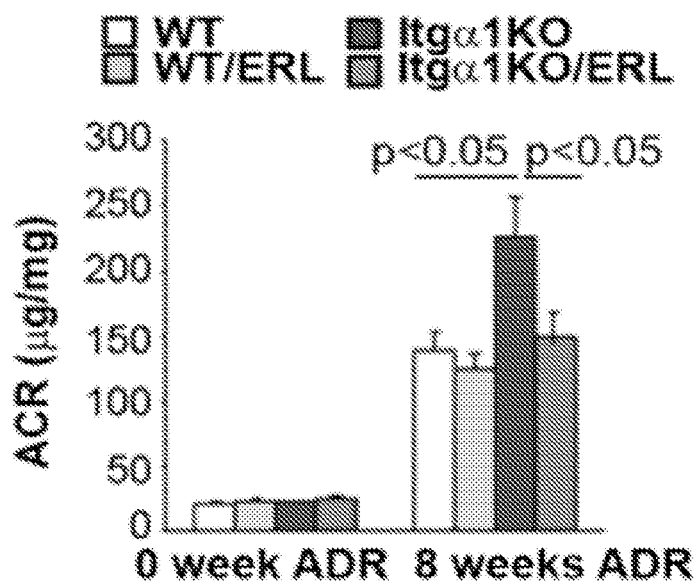
Figure 1D:
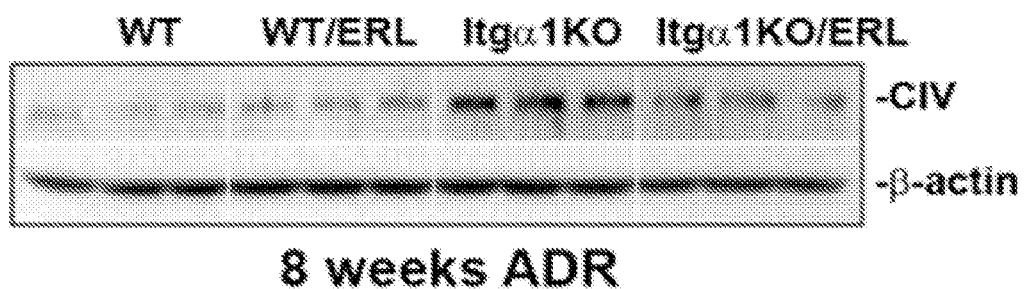
Figure 1E:
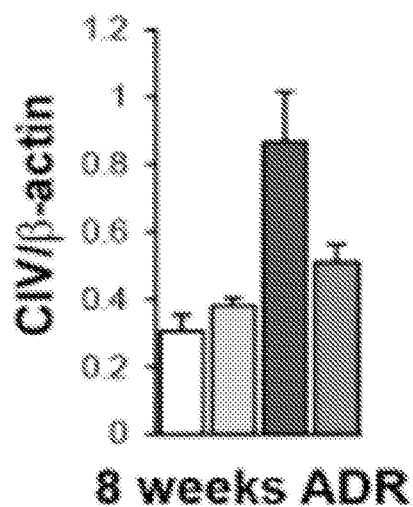
Figure 2A:
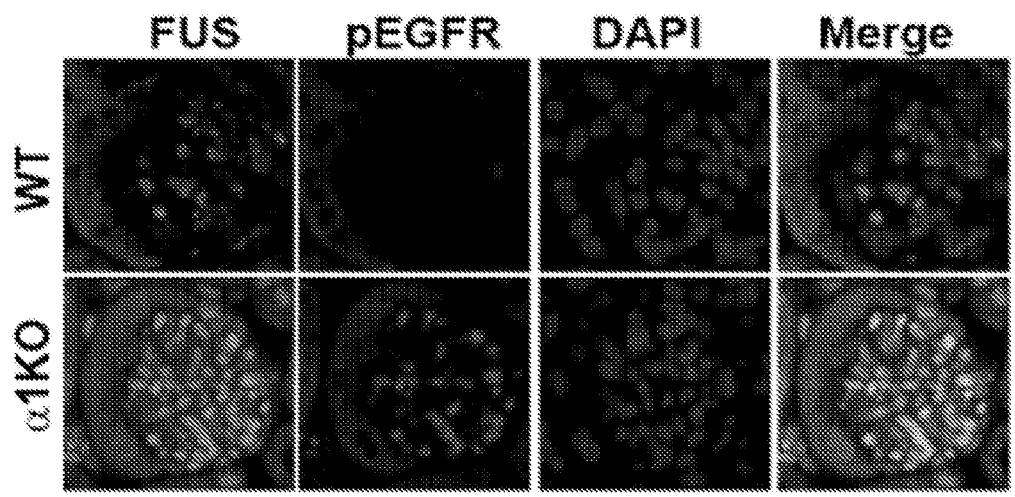
FIGS. 2A to 2D. (A, B) Kidney paraffin sections of the mice indicated were co-stained with anti-FUS (green) and anti-phospho EGFR (red) antibodies. Note that FUS is highly expressed and co-localize with phospho EGFR in the glomeruli of Itgα1KO mice (B mean±SEM of 10 glom/mice with 3 mice evaluated). (C, D) Nuclear fractionation of glomeruli isolated from 5 WT and 5 Itgα1KO mice showed significantly higher nuclear FUS levels in the Itgα1KO mice.
Figure 2B:
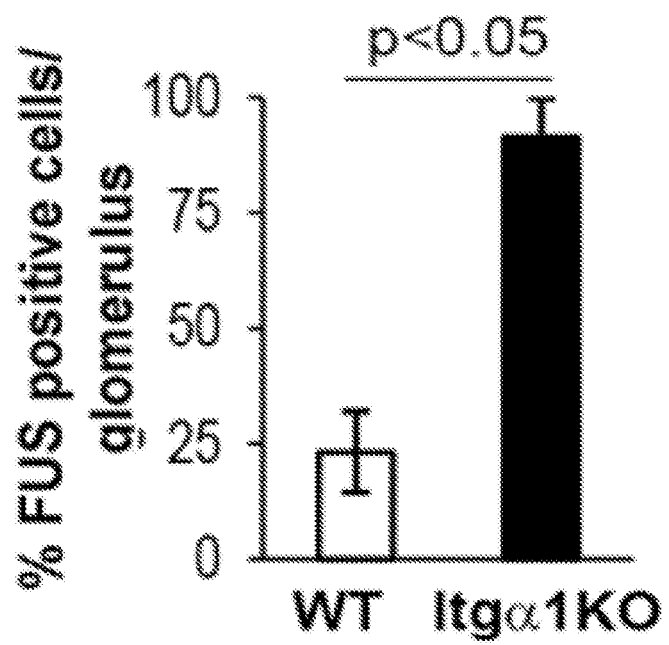
Figure 2C:
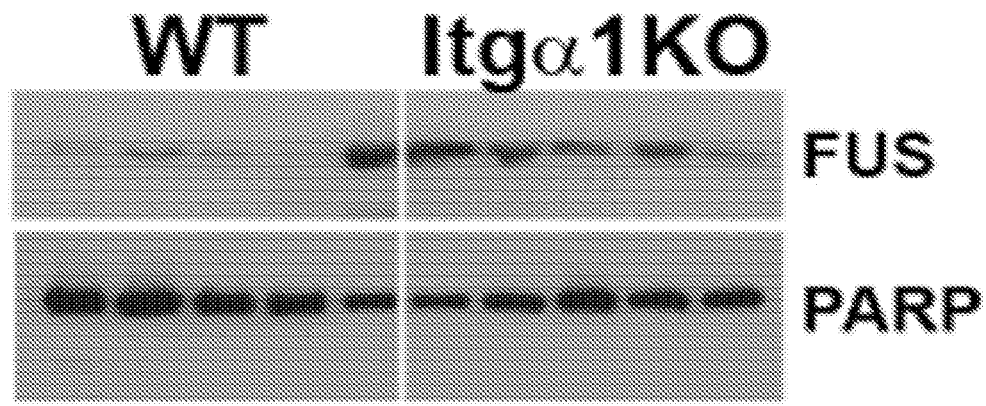
Figure 2D:
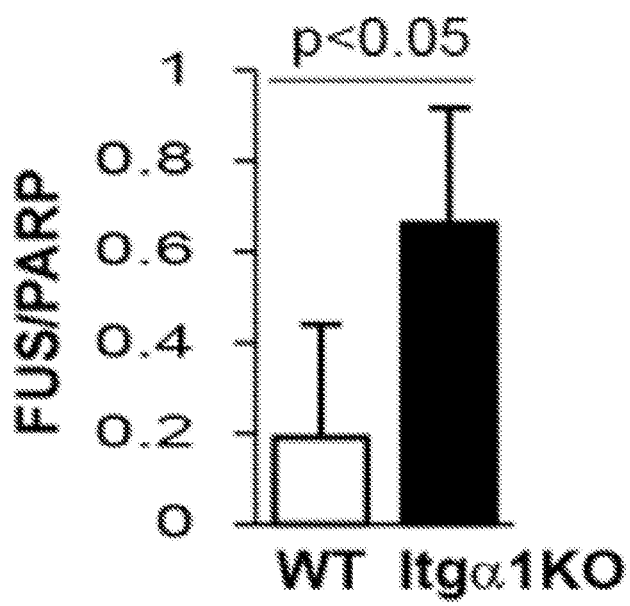

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "treatment" and "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The term "inhibit," "reduce," or "suppress" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "peptide," "polypeptide," and "protein" are used interchangeably to refer to a natural or synthetic molecule comprising two or more amino acids linked by the carboxyl group of one amino acid to the alpha amino group of another.

In addition, as used herein, the term "polypeptide" refers to amino acids joined to each other by peptide bonds or modified peptide bonds, e.g., peptide isoesters, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half-life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "protein domain" refers to a portion of a protein, portions of a protein, or an entire protein showing structural integrity; this determination may be based on amino acid composition of a portion of a protein, portions of a protein, or the entire protein.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino, acids.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The C terminal domain of FUS contains an uncommon nuclear localization sequence (NLS) motif called PY-NLS that binds the nuclear import receptor transportin. Phosphorylation of FUS leads to its association with transportin and nuclear translocation with consequent increased in collagen production. Therefore, disclosed herein is an isolated peptide (or peptidomimetic thereof) comprising a transportin-binding moiety, which inhibits FUS from binding transportin, linked to a membrane translocating motif. In some embodiments, the disclosed peptide has a binding affinity greater than about $10^5$ (e.g., $10^6$, $10^7$, $10^8$, $10^9$, $10^{10}$, $10^{11}$, and $10^{12}$ or more) moles/liter for transportin.

In some embodiments, the transportin-binding moiety comprises a C-terminal fragment of a FUS ribonucleoprotein. For example, the transportin-binding moiety can comprise the amino acid sequence SRGEHRQDRRERPY (SEQ ID NO:1), or a conservative variant thereof.

Non-limiting examples of membrane translocating motifs include Polyarginine (e.g., R9), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

In some embodiments, the membrane translocating motif comprises a signal sequence hydrophobic region (SSHR). For example, the SSHR can be derived from an integrin $\beta_3$ protein, such as a human integrin $\beta_3$ protein, or from a fibroblast growth factor 4 (FGF4) protein, such as a human FGF4 protein. In some embodiments, the membrane translocating motif comprises the amino acid sequence XXXXLLPXXLLALLAP (SEQ ID NO:2) or XXXXLLPXXLLAVLAP (SEQ ID NO:3), wherein X is any amino acid or absent. In some embodiments, the membrane translocating motif comprises the amino acid sequence AAVALLPAVLLALLAP (SEQ ID NO:4) or AAVALLPAVLLAVLAP (SEQ ID NO:5).

In some embodiments, the polypeptide comprises the amino acid sequence AAVALLPAVLLALLAP (SEQ ID NO: 3)-SRGEHRQDRRERPY (SEQ ID NO: 1) or AAVALLPAVLLAVLAP (SEQ ID NO: 4)-SRGEHRQDRRERPY (SEQ ID NO: 1), wherein "—" is a linker or peptide bond. Linkers can be short peptide sequences that occur between protein domains. The linkers can be flexible or rigid. Flexible linkers are often composed of flexible residues like glycine and serine so that the adjacent protein domains are free to move relative to one another. In particular, the linker can be a polyglycine (e.g. 3, 4, or 5 glycine), a polyserine (e.g. 3, 4, or 5 serine), or a combination of glycine and serine including repeating combinations. For example, the linker can be a glycine and serine linker, such as, for example, a G4S, GSG4, G2SG3SG2, G2SG, G3S linker, or any other linker known in the art where the base linker sequence can optionally be repeated 2, 3, 4, or more times. In some embodiments, the polypeptide comprises the amino acid sequence

```
                                        (SEQ ID NO: 8)
AAVALLPAVLLALLAPSRGEHRQDRRERPY
or
                                        (SEQ ID NO: 9)
AAVALLPAVLLAVLAPSRGEHRQDRRERPY.
```

The disclosed peptide can further include one or more additional moieties. For example, the peptide can contain a homing peptide or organ-specific or cell-specific Fab antibody fragment for targeted delivery to an organ, such as the lung, kidney, skin, heart, pancreas, uterus, retina, intestines, prostate, or liver. The peptide can also contain a label, such as a fluorescent dye. The methods for selecting homing peptides or Fab antibody fragments are available as described in several publications. For example, those skilled in the art can use published protocols in Korbelin J t al 2016 Mol. Therapy, 24(6):1050-1061), Pulmonary Targeting of Adeno-associated Viral Vectors by Next-generation Sequencing-guided Screening of Random Capsid Displayed peptide Libraries, Rosowski S et al Microb Cell Fact. 2018 Jan. 9; 17(1):3. doi: 10.1186/s12934-017-0853-z A novel one-step approach for the construction of yeast surface display Fab antibody libraries, and Kelly R L et al 2018 . Mol. Biol. 430(1):119-130,doi: J10.1016/j.jmb.2017.11.008. Epub 2017 Nov. 26. Examples of homing peptides include but are not limited to the lysine glutamine $(K2E3)_3K$ peptide which has renal specificity; CARSKNKDC (SEQ ID NO: 12) which has vascular specificity; and the lung homing peptide $X_1$-G-F-E-$X_2$(SEQ ID NO: 6), where $X_1$ and $X_2$ each is 1 to 10 independently selected amino acids including, for example, the sequence CGFECVRQCPERC (SEQ ID NO: 14) or CGFELETC (SEQ ID NO: 15). In some aspects, the disclosed peptide comprises the amino acid sequence

```
                                        (SEQ ID NO: 10)
XXXXLLPXXLLA$LAP-SRGEHRQDRRERPY,
``` wherein "X" is any naturally occuring amino acid,
wherein "$" is a valine or a leucine, and
wherein "—" is a linker or a peptide bond.

In some aspects, the disclosed peptide comprises the amino acid sequence

```
                                        (SEQ ID NO: 11)
AAVALLPAVLLA$LAP-SRGEHRQDRRERPY,
``` wherein "X" is any naturally occurring amino acid,
wherein "$" is a valine or a leucine, and
wherein "—" is a linker or a peptide bond.

In some aspects, the disclosed polypeptide comprises a conservative variant of a disclosed amino acid sequence. For example, in some aspects, the disclosed polypeptide comprises a disclosed amino acid sequence having 1, 2, 3, or 4 conservative amino acid substitutions.

The disclosed peptide can have a variety of lengths and structures as described herein. In some aspects, the disclosed peptide can consist essentially of from about 25 to about 100 amino acids, including about 25, 30, 35, 40, 45, 50, 55, 60, 65, 70, 75, 80, 85, 90, 95, 100, or more amino acids. The disclosed peptide can comprise less than about 100 amino acid residues, including less than about 100, 95, 90, 85, 80, 75, 70, 65, 60, 55, 50, 45, 40, 35, or 30 amino acid residues. The disclosed peptide can comprise more than about 25 amino acid residues, including more than about 25, 30, 35, 40, 45, or 50 amino acid residues.

The disclosed polypeptides can be artificial sequences and can be synthesized in vitro and/or recombinantly. The disclosed polypeptides can be peptides that are not naturally occurring proteins and can be peptides that have at least two contiguous sequences that are not contiguous in a naturally occurring protein.

Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics. Chimeric mutant proteins occur naturally when a large-scale mutation, typically a chromosomal translocation, creates a novel coding sequence containing parts of the coding sequences from two different genes.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins. This technique is often used for identification and purification of proteins, by fusing a GST protein, FLAG peptide, or a hexa-his peptide (aka: a 6×his-tag) which can be isolated using nickel or cobalt resins (affinity chromatography). Chimeric proteins can also be manufactured with toxins or anti-bodies attached to them in order to study disease development.

Alternatively, internal ribosome entry sites (IRES) elements can be used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; PCT/US99/05781). IRES sequences are known in the art and include those from encephalomycarditis virus (EMCV) (Ghattas, I. R. et al., Mol. Cell. Biol., 11:5848-5849 (1991); BiP protein (Macejak and Sarnow, Nature, 353:91 (1991)); the Antennapedia gene of drosophilia (exons d and e) [Oh et al., Genes & Development, 6:1643-1653 (1992)); those in polio virus [Pelletier and Sonenberg, Nature, 334:320325 (1988); see also Mountford and Smith, TIG, 11:179-184 (1985)).

The disclosed peptide can further include one or more additional moieties. For example, the peptide can contain a homing peptide for targeted delivery to an organ, such as the lung, kidney, skin, heart, pancreas, uterus, retina, intestines, prostate, or liver. The peptide can also contain a label, such as a fluorescent dye. In one aspect, the homing peptide can be an Fab antibody fragment specific for an organ-specific or cell-specific epitope (such as, for example, a cell-specific or organ-specific peptide, polypeptide, or protein). It is understood and herein contemplated that by "organ-specific" and "cell-specific" epitope is meant an epitope (such as, for example, a peptide, polypeptide, or protein) whose expression is limited to that cell-type or organ.

Therapeutic molecules, such as the polypeptides disclosed herein, can be used therapeutically in combination with a pharmaceutically acceptable carrier. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Pharmaceutical carriers suitable for administration of the molecules provided herein include any such carriers known to those skilled in the art to be suitable for the particular mode of administration. Pharmaceutical compositions may include thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Liquid pharmaceutically administrable compositions can, for example, be prepared by dissolving, dispersing, or otherwise mixing a molecules as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

The compounds described herein can be formulated for parenteral administration. Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations can be designed for immediate release, sustained release, delayed release and/or burst release of one or more polypeptides in a therapeutically effective amount. In a preferred embodiment, the formulation provides an initial burst release of a "loading dosage", followed by a sustained release to maintain the therapeutically effective dosage. This can be accomplished using a delayed and/or extended release formulation.

Disclosed herein are methods for reducing, inhibiting, preventing, or treating a fibrotic disease in a subject comprising administering to the subject a therapeutically effective amount of a composition comprising an agent that inhibits nuclear translocation of Fused in Sarcoma (FUS). Similarly, disclosed herein are methods for reducing, inhibiting, preventing, or treating FUS-mediated collagen production by a cell comprising administering to the subject a therapeutically effective amount of a composition comprising an agent that inhibits nuclear translocation of Fused in Sarcoma (FUS). It is understood and herein contemplated that the agent for reducing, inhibiting, preventing, or treating a fibrotic disease or FUS collagen production can be any isolated peptides disclosed herein comprising a transportin-binding moiety linked to a membrane translocating motif.

As disclosed herein, fibrotic diseases can include, but are not limited to pulmonary fibrosis (including, cystic fibrosis and radiation induced lung injury), atrial fibrosis, glomerulosclerosis, kidney damage, skin fibrosis (scleroderma), scleroderma from a systemic fibrosis, cirrhosis, Crohn's Disease, Keloid, Myelofibrosis, arthrofibrosis, fibrosarcoma, osteosarcoma tumor, or collagen production by a tumor.

In particular embodiments, the method involves administering a polypeptide disclosed herein. For example, the disclosed polypeptides can in some cases be administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of polypeptide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

In some embodiments, the dose of polypeptide to be administered provides a final plasma level of polypeptide of about 100 ng/ml to about 1000 ng/ml, about 1100 ng/ml to about 1450 ng/ml, 100 ng/ml to about 250 ng/ml, about 200 ng/ml to about 350 ng/ml, about 300 ng/ml to about 450 ng/ml, about 350 ng/ml to about 450 ng/ml, about 400 ng/ml to about 550 ng/ml, about 500 ng/ml to about 650 ng/ml, about 600 ng/ml to about 750 ng/ml, about 700 ng/ml to about 850 ng/ml, about 800 ng/ml to about 950 ng/ml, about 900 ng/ml to about 1050 ng/ml, about 1000 ng/ml to about 1150 ng/ml, about 100 ng/ml to about 1250 ng/ml, about 1200 ng/ml to about 1350 ng/ml, about 1300 ng/ml to about 1500 ng/ml.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, transdermally, or topically.

The disclosed composition can be administered therapeutically, to treat, prevent, or reduce fibrotic disease or FUS-mediated collagen production in a subject or prophylactically, to patients or subjects at risk for fibrosis. Accordingly, the compositions may be administered prior to the onset of fibrosis (including, for example, prior to exposure to radiation which could result in fibrotic injury). In one aspect, the disclosed compositions can be administered to the patient or subject as a single one time injection or as multiple administrations. For example, the disclosed compositions can be administered at least 1, 2, 3, 4, 5, 6, 7, 8, 9, 10, 11, or 12 times per day. The compositions can be administered to the patient or subject at least once about every 4, 6, 8, 12, 24 hours, or every day, every other day, every third day, every fourth day, every fifth day, every sixth day, once a week, once every two weeks, once every three weeks, once a month, once every two months, once every three months, once every four months, once every five months, once every six months, once every seven months, once every eight months, once every nine months, once every ten months, once every eleven months, once every year, once every eighteen months, once every two year, once every three years, once every four years, or once every five years. Treatment can be continued as long as needed to reduce, inhibit, prevent, or eliminate the fibrotic disease or symptoms associated with the disease.

The disclosed polypeptides can be administered adjunctively with other active compounds such as analgesics, anti-inflammatory drugs, antipyretics, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, doparninergics, electrolytes, parasympathomimetics, stimulants, anorectics and anti-narcoleptics.

As noted above, the compositions disclosed herein may be administered prophylactically to patients or subjects who are at risk for fibrosis. Thus, the method can further comprise identifying a subject at risk for fibrosis prior to administration of the herein disclosed compositions.

A number of embodiments of the invention have been described.

Nevertheless, it will be understood that various modifications may be made without departing from the spirit and scope of the invention. Accordingly, other embodiments are within the scope of the following claims.

EXAMPLES

Example 1

Integrins are transmembrane receptors for ECM components composed of non-covalently bound α and β subunits that heterodimerize to produce 24 different transmembrane receptors (Hynes, R. 2002. Cell 110:673-687; Pan, L., et al. 2016. Springerplus 5:1094). Integrin α1β1 (Itgα1β1) is a major collagen IV receptor that is highly expressed by podocytes, endothelial cells and mesangial cells of the glomerulus (Patey, N., et al. 1994. Cell Adhes Commun 2:159-167). Absence of Itgα1β1 does not affect the normal glomerular function; however, this integrin plays an important role in regulating the glomerular response to injury. Itgα1β1 has been identified as a negative, inhibitory, modulator of glomerular injury. To this end, Itgα1β1 prevents excessive injury-mediated glomerulosclerosis by negatively regulating EGF receptor (EGFR) tyrosine phosphorylation, by preventing the assembly of the NADPH oxidase and generation of profibrotic ROS, and by negatively regulating collagen levels at both translational and transcriptional levels (Chen, X., et al. 2007. Mol Cell Biol 27:3313-3326; Chen, X., et al. 2004. Am J Pathol 165:617-630; Chen, X., et al. 2010. Mol Cell Biol 30:3048-3058; Wang, H., et al. 2015. Kidney Int 87:948-962; Gardner, H., et al. 1999. J Cell Sci 112:263-272). Itgα1β1 exerts its anti-fibrotic role by regulating both the level and tyrosine phosphorylation of caveolin-1 a scaffolding protein that controls EGFR activation (Chen, X., et al. 2010. Mol Cell Biol 30:3048-3058; Borza, C. M., et al. 2010. J Biol Chem 285:40114-40124). TGF-β receptor II has also been identified as another target of Itgα1β1. Itgα1β1 also negatively regulates TGF-β receptor II-mediated SMAD3 activation and pro-fibrotic signaling by downregulating the tyrosine phosphorylation levels of TGF-β receptor II (Chen, X., et al. 2014. J Clin Invest 124:3295-3310).

A mechanism whereby Itgα1β1 negatively regulates the tyrosine phosphorylation levels of several growth factor receptors as well as scaffolding proteins is by recruiting and activating the tyrosine phosphatase TCPTP (Mattila, E., et al. 2005. Nat Cell Biol 7:78-85). Consistent with this finding, cells lacking Itgα1β1 do not recruit and activate TCPTP thus showing increased basal levels of tyrosine phosphorylated proteins (Chen, X., et al. 2007. Mol Cell Biol 27:3313-3326). Mice lacking Itgα1β1 manifest excessive and accelerated glomerulosclerosis following various models of glomerular injury, including partial renal ablation, adriamycin injection, oxidative stress, and type 1 diabetes (Chen, X., et al. 2004. Am J Pathol 165:617-630; Wang, H., et al. 2015. Kidney Int 87:948-962; Borza, C. M., et al. 2012. J Am Soc Nephrol 23:1027-1038; Zent, R., et al. 2006. Kidney Int 70:460-470; Yu, L., et al. 2012. Kidney Int 81:1086-1097).

A key question is how Itgα1β1, in addition to the targets indicated above, controls collagen levels at the transcriptional level. The activation of many transcription factors and their nuclear translocation are regulated by tyrosine phosphorylation (Rebelo, S., et al. 2015. Cell Signal 27:2589-2598; Thapar, R. 2015. ACS Chem Biol 10:652-666). Thus, immunoprecipitation of nuclear proteins from wild type (WT) and Itgα1KO mesangial cells was performed using anti-phosphotyrosine antibody. The complexes were analyzed by mass spectrometry in order to identify highly tyrosine phosphorylated nuclear proteins only in Itgα1KO cells. As disclosed herein, increased levels of total and tyrosine phosphorylated nuclear ribonucleoprotein Fused in Sarcoma (FUS) in Itgα1KO cells are associated with increased collagen production, and reducing FUS levels diminishes collagen production. Thus, Itgα1β1 plays an anti-fibrotic action by decreasing the tyrosine phosphorylation and nuclear levels of FUS.

EGFR is a receptor tyrosine kinase activated by several ligands including EGF, TGF-α, and HB-EGF. This receptor is expressed by mesangial cells and podocytes and plays an important role in the development of the kidney (Zhuang, S., et al. 2014. Kidney Int Suppl (2011) 4:70-74). In addition, EGFR is a key determinant in the initiation, development and progression of kidney glomerular injury. In the ⅚ nephrectomy model, for example, inhibition of EGFR reduces glomerular fibrosis suggesting that activation of EGFR occurs in the course of glomeruli injury and contributes to fibrosis (Liu, N., et al. 2012. PLoS ONE 7:e36194). In both mice and humans with rapidly progressive glomerulonephritis expression of HB-EGF by podocytes promotes EGFR phosphorylation and activation thus contributing to glomerular injury (Bollee, G., et al. 2011. Nat Med 17:1242-1250). In addition, mice lacking HB-EGF expression specifically in endothelial cells, show decrease glomerular EGFR activation and decreased angiotensin-II mediated glomerular injury (Zeng, F., et al. 2016. Am J Physiol Renal Physiol:ajprenal 311(4):F695-F707).

A key negative regulator of EGFR activation and profibrotic function is Itgα1β1. At least two mechanisms account for this negative regulation: Itgα1β1 binds and activates TCPTP and interacts with the membrane scaffolding protein caveolin 1, two negative regulators of EGFR activation (Chen, X., et al. 2010. Mol Cell Biol 30:3048-3058; Borza, C. M., et al. 2010. J Biol Chem 285:40114-40124; Borza, C. M., et al. 2010. J Biol Chem 285:40114-40124; Abulrob, A., et al. 2004. Oncogene 23:6967-6979). To further determine the contribution of EGFR to glomerular injury in Itgα1KO mice, a genetic and a pharmacological approach was used.

In the first model, Itgα1KO mice were crossed with mice expressing a functionally hypomorphic EGFR (waved-2 mice) (Luetteke, N.C., et al. 1994. Genes Dev 8:399-413) and then subjected to adriamycin (ADR)-mediated injury. In the second model, wild type (WT) and Itgα1KO mice were injected with ADR and then left untreated or treated with the EGFR inhibitor erlotinib (20 mg/Kg/day i.p.). Compared to WT mice, Itgα1KO mice developed significantly more glomerular injury, proteinuria and glomerular collagen synthesis 8 weeks after ADR treatment (FIG. 1A-E). Crossing the Itgα1KO mice with the wave-2 mice or treating them with erlotinib significantly improved glomerular injury, proteinuria and collagen synthesis (FIG. 1A-E).

Although this data suggests that blocking EGFR with available receptor tyrosine kinase inhibitors might be a promising strategy for the treatment and management of glomerular injury, it is important to notice that prolonged treatment with receptor kinase inhibitors, including erlotinib, can cause some severe side effects. The most common side effects include skin rash, cardiovascular and pulmonary toxicities, electrolyte depletion, diarrhea and renal complications (reviewed in (Liu, F., et al. 2016. Int J Mol Sci 17). Thus, the identification of key downstream signaling molecules activated by the integrins/EGFR axis or integrins alones, might represent a valid tool to better target kidney disease and avoid severe side effects. In this regard, FUS is shown herein to contain Tyr6 and Tyr296 as two EGFR phosphorylatable and TCPTP dephosphorylatable tyrosines. In addition, levels of nuclear FUS seem to be associated with levels of activated EGFR.

FUS, also known as translocated in liposarcoma (TLS), is a heterogeneous ribonucleoprotein able to bind RNA and proteins (Sama, R. R., et al. 2014. ASN Neuro 6). FUS consists of an N-terminal end involved in transcriptional activation and a C-terminal end involved in protein-RNA and protein-protein interactions (Sama, R. R., et al. 2014. ASN Neuro 6). The C terminal domain also contains an uncommon nuclear localization sequence (NLS) motif called PY-NLS because the PY is localized at the C-terminus of the protein. The PY-NLS binds the nuclear import receptor transportin (or karyopherin β2) (Dormann, D., et al. 2010. Embo J 29:2841-2857). In 2009, two groups analyzed several unrelated families who presented with amyotrophic lateral sclerosis (ALS) phenotype and found 14 mutations in the FUS gene, thus providing the first evidence that FUS is linked to familiar ALS (Kwiatkowski, T. J., Jr., et al. 2009. Science 323:1205-1208; Vance, C., et al. 2009. Science 323:1208-1211). Indeed, mutations in the C-terminal domain of FUS that prevent nuclear translocation thus causing increased cytoplasmic localization and formation of stress granule-like structures account for ~5% of familiar ALS cases (reviewed in (Sama, R. R., et al. 2014. ASN Neuro 6). In addition to mutations, overexpression of FUS can also be pathogenic in human patients (Sabatelli, M., et al. 2013. Hum Mol Genet 22:4748-4755). After these findings, mouse models of ALS overexpressing FUS or carrying the same FUS mutations identified in humans have been generated (Picher-Martel, V., et al. 2016. Acta Neuropathol Commun 4:70). Mice have been generated that express human FUSWT or the pathological mutation FUSR521G (no longer able to translocate to the nucleus) under the control of the cytomegalovirus immediate early enhancer-chicken β-actin hybrid promoter. These mice express wild type or mutated FUS only when crossed with a Cre mouse line. When crossed with a global Cre mouse line, thus forcing expression of these two proteins in all cells, these mice are born alive but develop severe motor deficits phenocopying the human diseases (Sephton, C. F., et al. 2014. Proc Natl Acad Sci U.S.A. 111:E4769-4778). These mice have been crossed with PDGFR-Cre mice in order to drive expression of WT and mutated form of FUS preferentially in mesangial cells. FUShet mice were also obtained. While FUSKO mice die immediately after birth on a C57/B6 background (Hicks, G. G., et al. 2000. Nat Genet 24:175-179), their survival rate increases on the BALB/c background. These mice are used to analyze the contribution of FUS in the regulation of collagen production in both physiological and pathological conditions.

Increased Nuclear Phosphorylated FUS in Itgα1KO Mesangial Cells.

A key question is to understand the molecular mechanisms whereby Itgα1β1 controls collagen levels at the transcriptional level. The nuclear translocation and activation of many transcription factors are processes regulated by tyrosine phosphorylation (Rebelo, S., et al. 2015. Cell Signal 27:2589-2598; Thapar, R. 2015. ACS Chem Biol 10:652-666). Cells lacking Itgα1β1 have increased basal levels of tyrosine phosphorylated proteins (e.g., EGFR, TGFβ receptor II and caveolin-1) (Chen, X., et al. 2007. Mol Cell Biol 27:3313-3326; Borza, C. M., et al. 2010. J Biol Chem 285:40114-40124; Chen, X., et al. 2014. J Clin Invest 124:3295-3310) due to inability to recruit and activate the tyrosine phosphatase TCPTP (Mattila, E., et al. 2005. Nat Cell Biol 7:78-85). In order to identify highly tyrosine phosphorylated nuclear proteins only in Itgα1KO, but not wild type (WT) cells, immuno-precipitation of nuclear proteins from WT and Itgα1KO mesangial cells was performed using anti-phosphotyrosine antibody and the complexes analyzed by mass spectrometry. Five potential hits were identified with 1 of them being the ribonucleoprotein Fused in Sarcoma (FUS).

FUS is a Ribonucleoprotein Regulated by TCPTP and EGFR.

FUS is a RNA-protein binding molecule that consists of an N-terminal end involved in transcriptional activation and a C-terminal end involved in protein and RNA binding. The rationale for selecting this candidate for study is as following: 1) FUS binds Sp1 (Dhar, S. K., et al. 2014. Antioxid Redox Signal 20:1550-1566) a transcriptional activator involved in collagen synthesis and fibrosis (Ghosh, A. K., et al. 2013. Exp Biol Med (Maywood) 238:461-481). 2) Patients with ALS show decreased levels of collagen in skin and blood (34, 35). 3) Collagen IV is a multimeric protein composed of 3 α subunits. These subunits are encoded by 6 different genes (α1-α6), each of which can form a triple helix with 2 other subunits to form type IV collagen. The α1 and α2 chains form the α1α2α1 type IV collagen and their transcription is regulated by a bidirectional promoter (846 bp) and a enhancer (329 bp) located in the first intron of the α1(IV) chain gene (Burbelo, P. D., et al. 1988. Proc Natl Acad Sci USA 85:9679-9682). Analysis of the murine enhancer and promoter sequence with ALGGEN-PROMO-v3 revealed the presence of 4 and 9 FUS responsive element in the enhancer and promoter, respectively. 4) FUS has 36 tyrosines and analysis of FUS with PhosphoMotif Finder revealed Tyr6 and Tyr296 as two EGFR phosphorylatable and TCPTP dephosphorylatable tyrosines. 5) Studies in *Drosophila* suggest a genetic link between Cabeza (orthologue of human FUS) and rhomboid-1, a key component of the EGFR signaling pathway (Shimamura, M., et al. 2014. Exp Cell Res 326:36-45). 6) Data shown below clearly suggest a link between nuclear localization of FUS and collagen synthesis.

Increased Levels of FUS in Itgα1KO Glomeruli.

To validate the mass spectrometry analysis, the nuclear levels of FUS in glomeruli from WT and Itgα1KO mice was analyzed. Nuclear FUS was detected in the glomeruli of both WT and Itgα1KO mice, although it was significantly more in the latter group (FIG. 2A-D). Interestingly nuclear FUS was found to localize with activated EGFR, which was evident only in glomeruli of Itgα1KO, but not WT mice (FIG. 2A) supporting the finding of increased basal level activation of EGFR in the absence of Itgα1β1 (Chen, X., et al. 2010. Mol Cell Biol 30:3048-3058).

Increased Glomerular FUS Expression in Human and Mouse Diseased Kidneys.

Figure 3A:
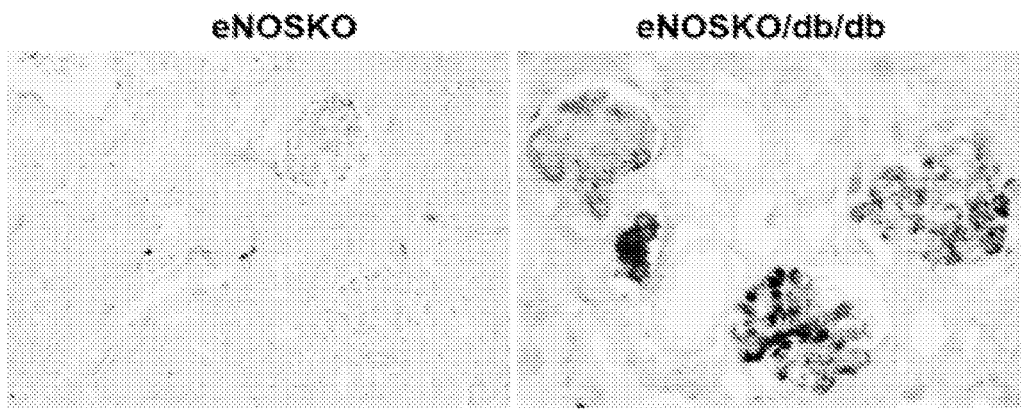
FIGS. 3A to 3C. (A) Kidney paraffin sections of eNOSKO or eNOSKO mice crossed with a mouse model of type 2 diabetes (db/db) were stained with anti-FUS antibody. Note the presence of FUS in the glomeruli of diabetic mice only (24 weeks old mice). (B,C) BALB/c WT mice were injected with adriamycin and then sacrificed at the time indicated. Nuclear fractions from isolated glomeruli blotted with anti-FUS or anti-HDAC2 (as loading control) (C, mean±SEM of 6 mice/treatment).
Figure 3B:
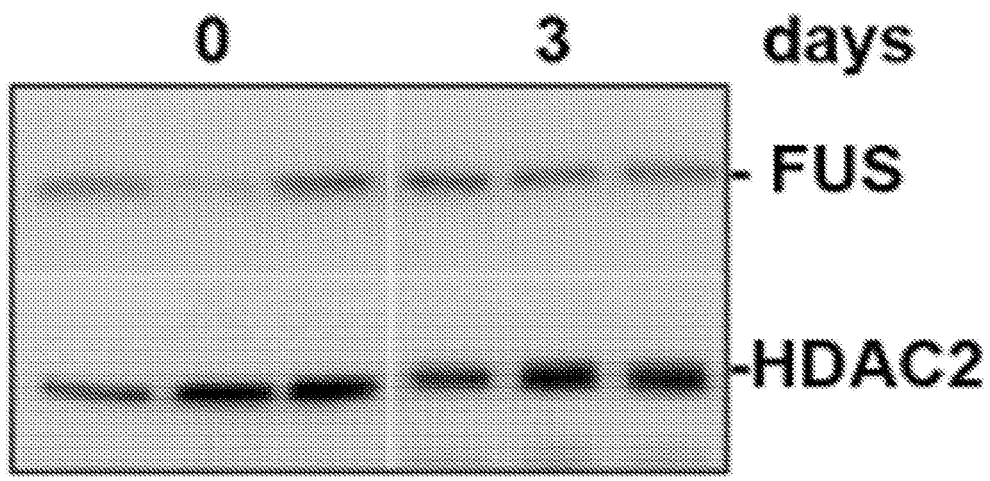
Figure 3C:
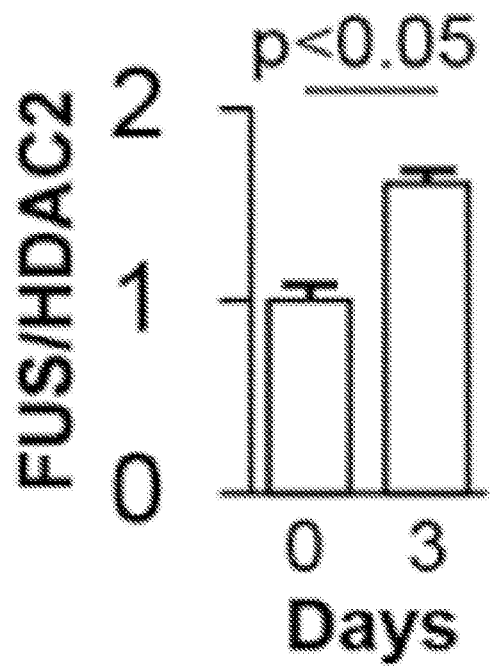

To determine whether levels of glomerular FUS are increased in kidney disease, FUS levels were analyzed in the glomeruli of control and type 2 diabetic mice. While no expression of this ribonucleoprotein was detected in the glomeruli of non-diabetic mice, FUS expression became evident in the glomeruli of type 2 diabetic mice (FIG. 3A). To further confirm that the levels of FUS increase following injury, WT mice were treated with Adriamycin (ADR) and a significant increase in nuclear FUS levels was observed in glomeruli isolated 3 days after ADR treatment (FIG. 3B,C). Interestingly, analysis of kidneys from healthy human subjects or individuals with early and late diabetic nephropathy, revealed expression of nuclear FUS only in the glomeruli of diabetic subjects, clearly suggesting that FUS is upregulated in kidney disease.

Increased FUS Nuclear Levels Directly Correlate to Collagen Synthesis.

Figure 4A:
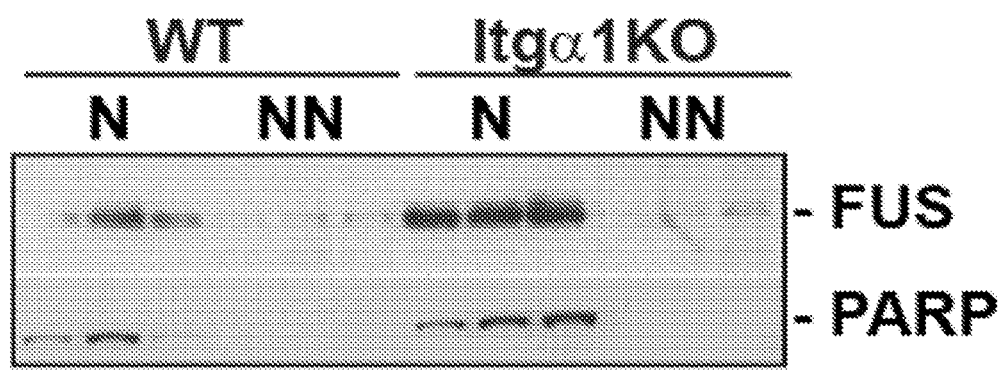
FIGS. 4A to 4C. (A, B) Nuclear (N) and non-nuclear (NN) fractions of WT and Itgα1KO mesangial cells showing significantly higher levels of FUS in the nuclei of Itgα1KO cells. (B, mean±SEM of 6 samples). (C) Non-nuclear and nuclear fractions were immuno-precipitated with the anti-pY antibody 4G10 or IgG control and then analyzed by Western Blot for levels of FUS. Note that tyrosine phosphorylated FUS is detected primarily in the nuclei of Itgα1KO cells.
Figure 4B:
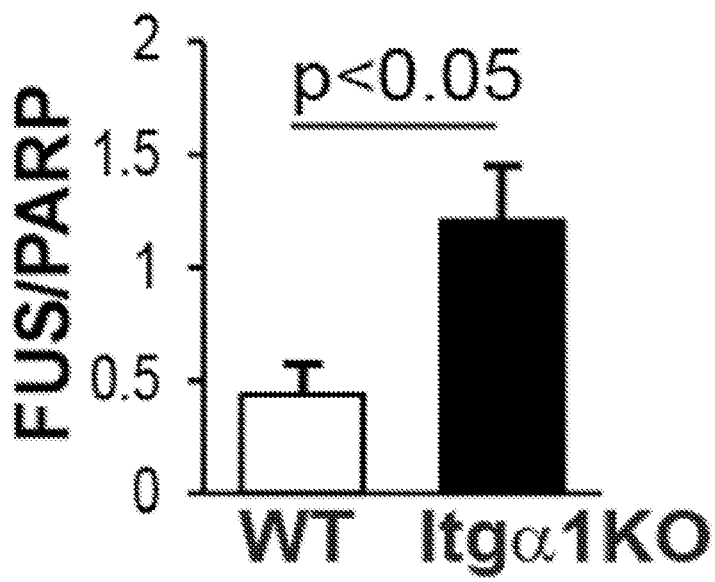
Figure 4C:
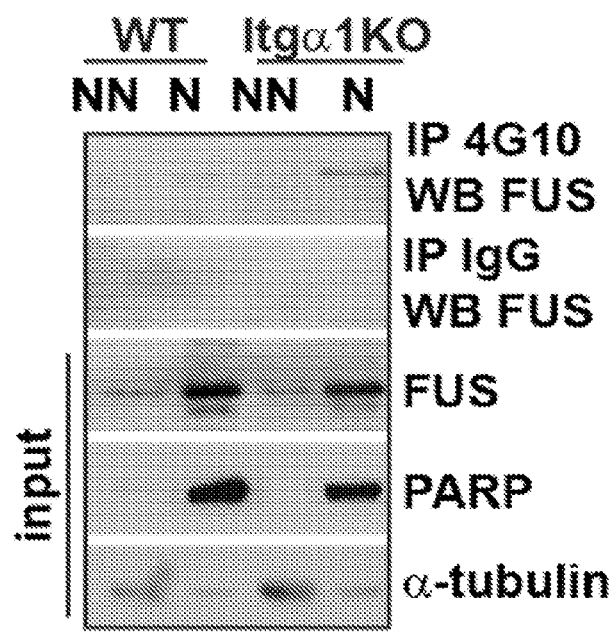
Figure 5A:
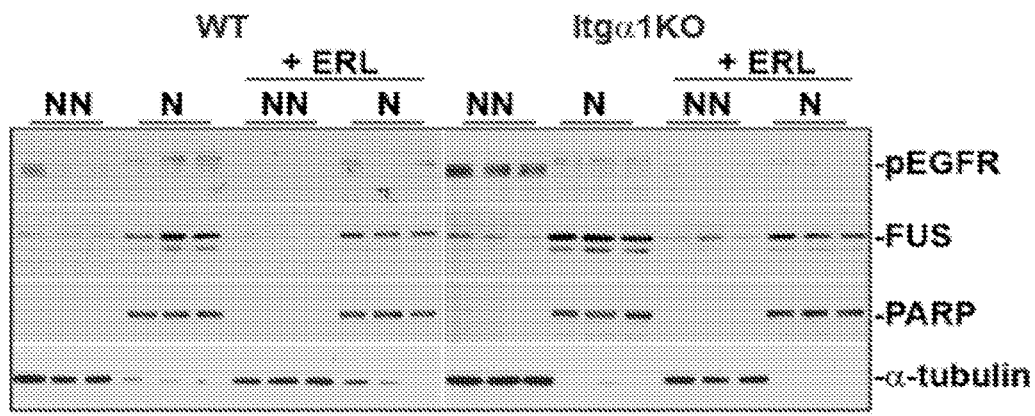
FIGS. 5A to 5F. WT and Itgα1KO mesangial cells were either kept untreated or treated with erlotinib (ERL) and the levels of phospho EGFR (A, B), nuclear FUS (A, C), collagen IV (D, E) and nuclear phosphorylated FUS (F,) were analyzed by Western blot. In Itgα1KO cells, ERL significantly decreased EGFR activation, nuclear FUS levels, collagen IV levels and tyrosine phosphorylated FUS. (B, C mean±SEM of 6 samples). NN=non-nuclear; N=nuclear.
Figure 5B:
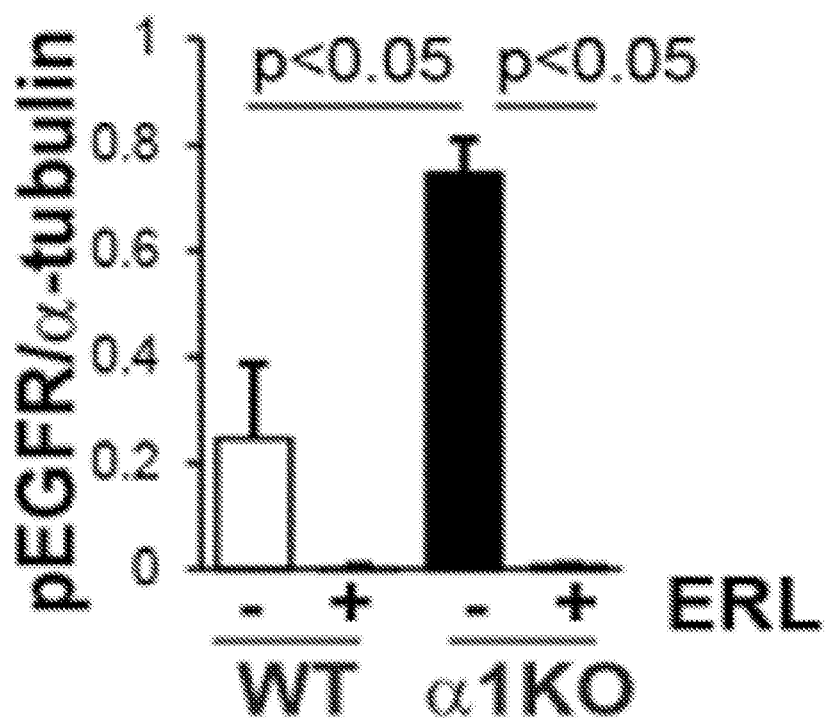
Figure 5C:
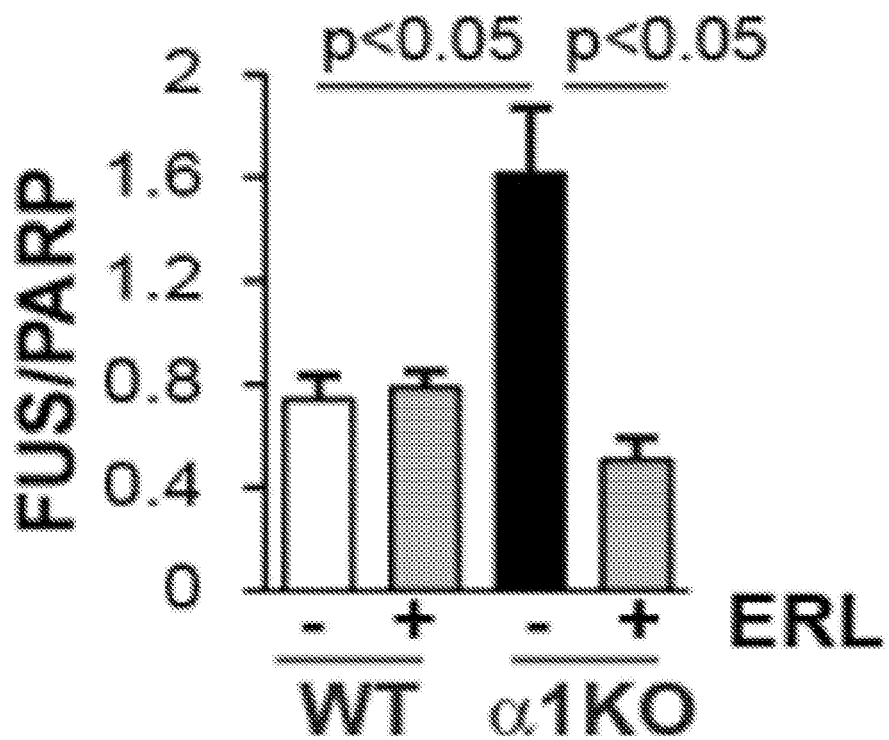
Figure 5D:
Figure 5E:
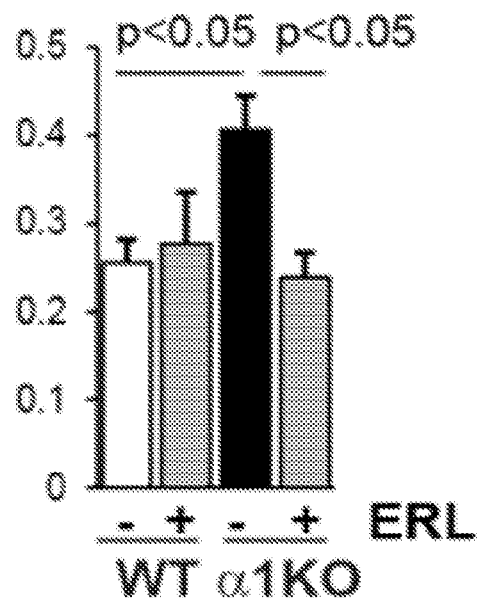
Figure 5F:
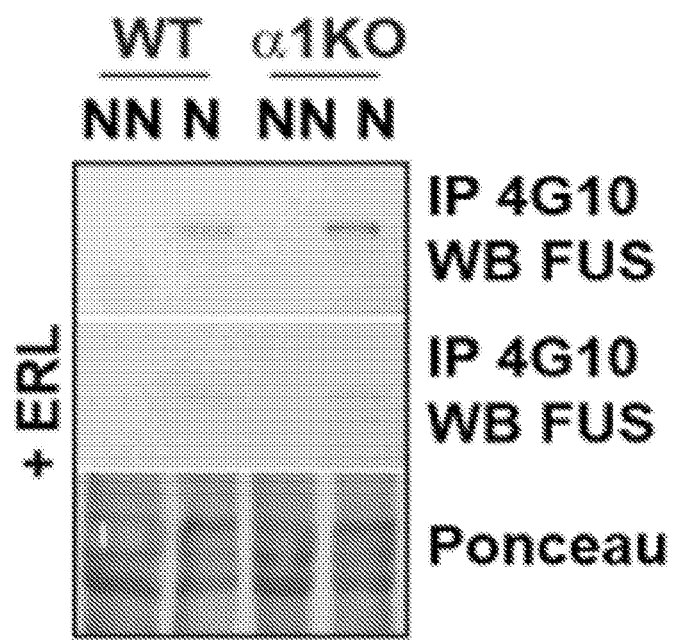

To further confirm the in vivo data, mesangial cells were isolated from WT and Itgα1KO mice and the basal level of nuclear FUS was analyzed. FUS was detected in the nuclei of both WT and Itgα1KO mesangial cells, although its levels were higher and more tyrosine phosphorylated in the latter group (FIG. 4A-C). To determine whether nuclear translocation of FUS is dependent on EGFR activation, mesangial cells were treated with erlotinib. This EGFR inhibitor decreased EGFR activation (5A,B) and significantly decreased nuclear FUS (FIG. 5A,C) and collagen IV levels (FIG. 5D,E), and these events were more pronounced in Itgα1KO mesangial cells. Treatment with erlotinib also significantly decreased the levels of nuclear tyrosine phosphorylated FUS (FIG. 5F), suggesting a potential link between EGFR activation, FUS phosphorylation and nuclear FUS localization.

FUS Nuclear Translocation is Dependent Upon EGFR Activation.

Figure 6A:
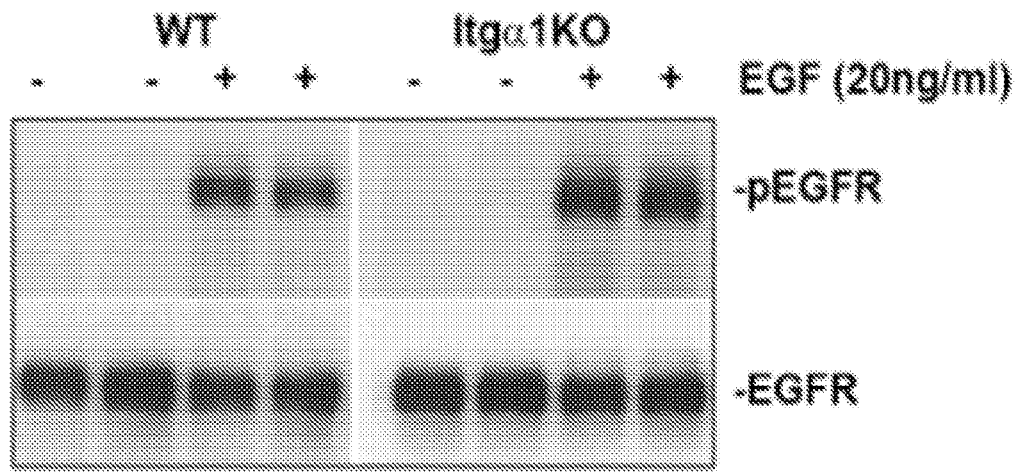
FIGS. 6A to 6F. WT and Itgα1KO mesangial cells were treated with EGF for 0 or 30 minutes. The levels of phospho-EGFR and EGFR were then analyzed by Western blot (A) and quantified by densitometry analysis (B, mean SEM of 6 samples). (C) WT (W) and Itgα1KO (K) cells were transiently transfected with RFP or RFP-FUS cDNA and levels of endogenous FUS and RPF-FUS were analyzed by Western blot with anti-RFP or anti-FUS antibody. (D) RFP-FUS transfected cells were treated with EGF for 0 or 30 minutes and then nuclear RFP-FUS (counterstaining with DAPI) was evaluated. (E) The number of RFP-FUS and DAPI cells per microscopic field was counted and expressed as RFP-FUS/DAPI (mean±SEM of 150 cells). WT and Itgα1KO mesangial cells were treated with EGF for 0 or 24 hours. The levels of Collagen IV and AKT (as loading control) were analyzed by Western blot and quantified by densitometry analysis (F, mean±SEM of 3 samples).
Figure 6B:
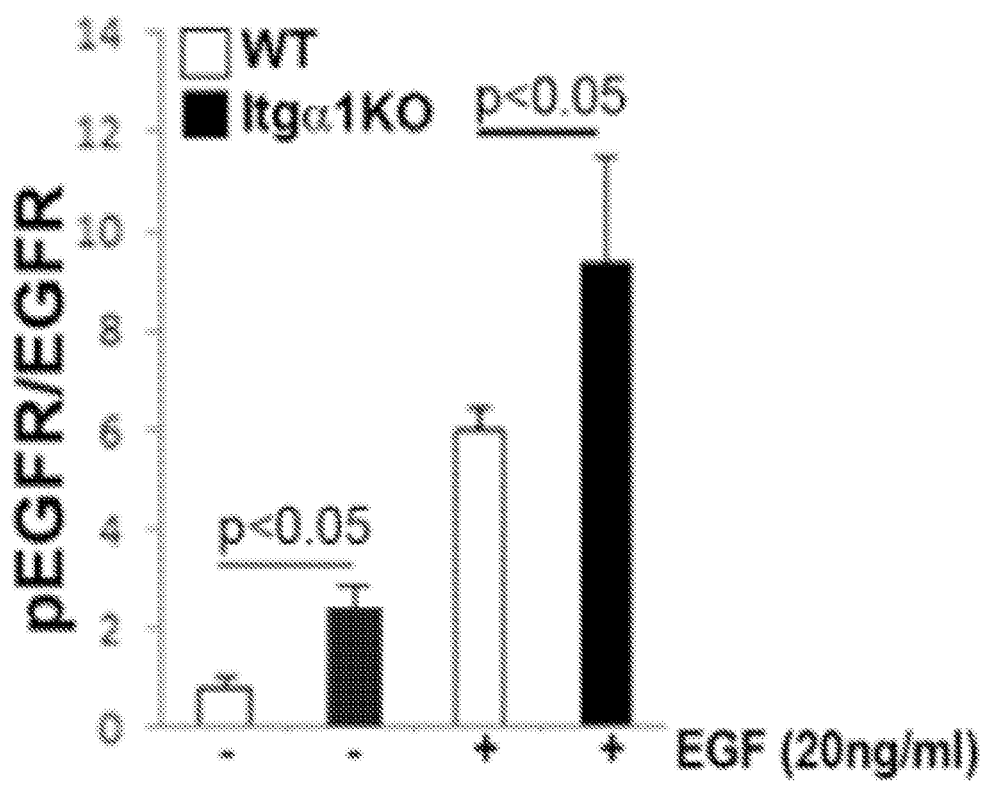
Figure 6C:
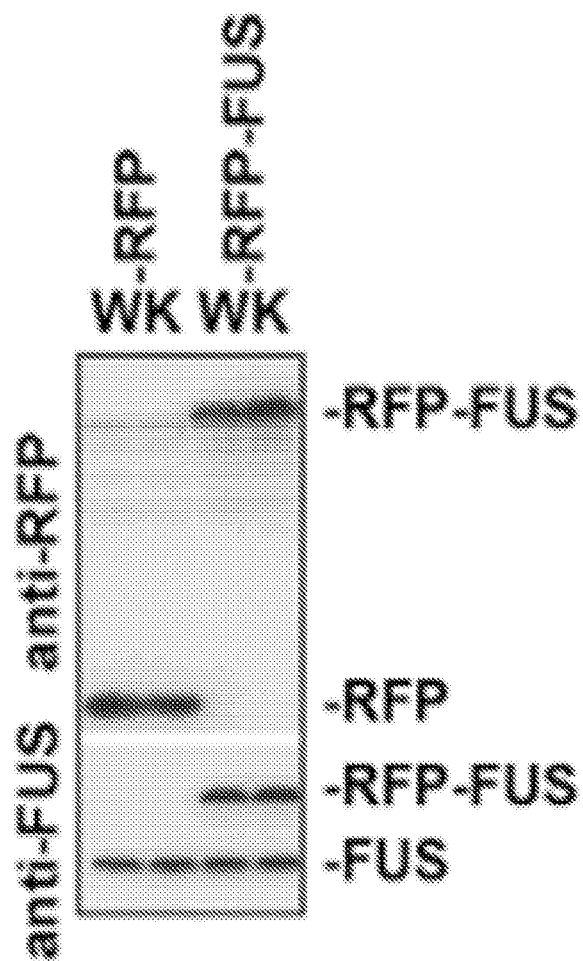
Figure 6D:
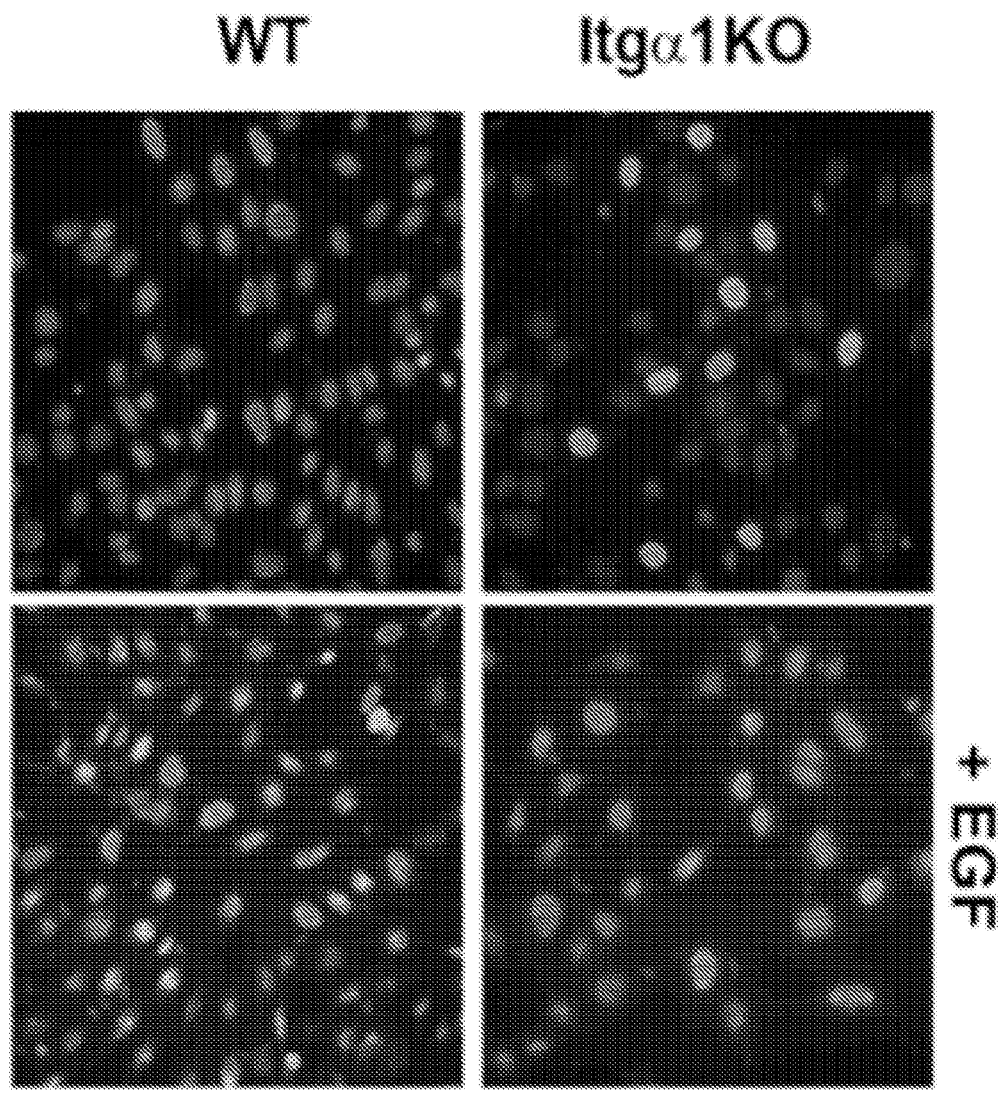
Figure 6E:
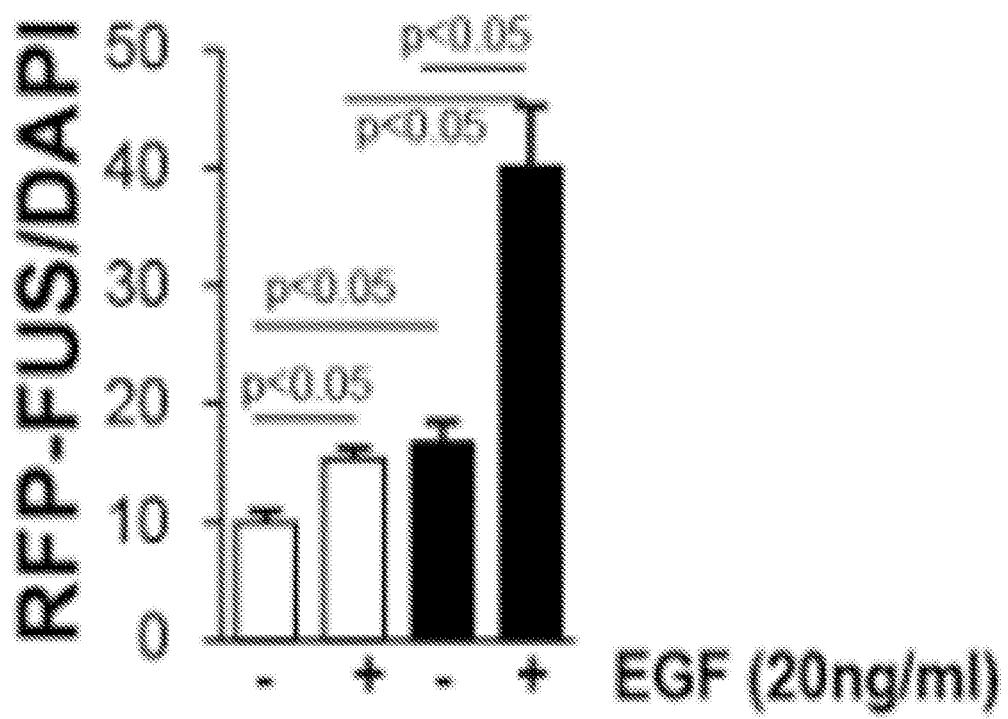
Figure 6F:
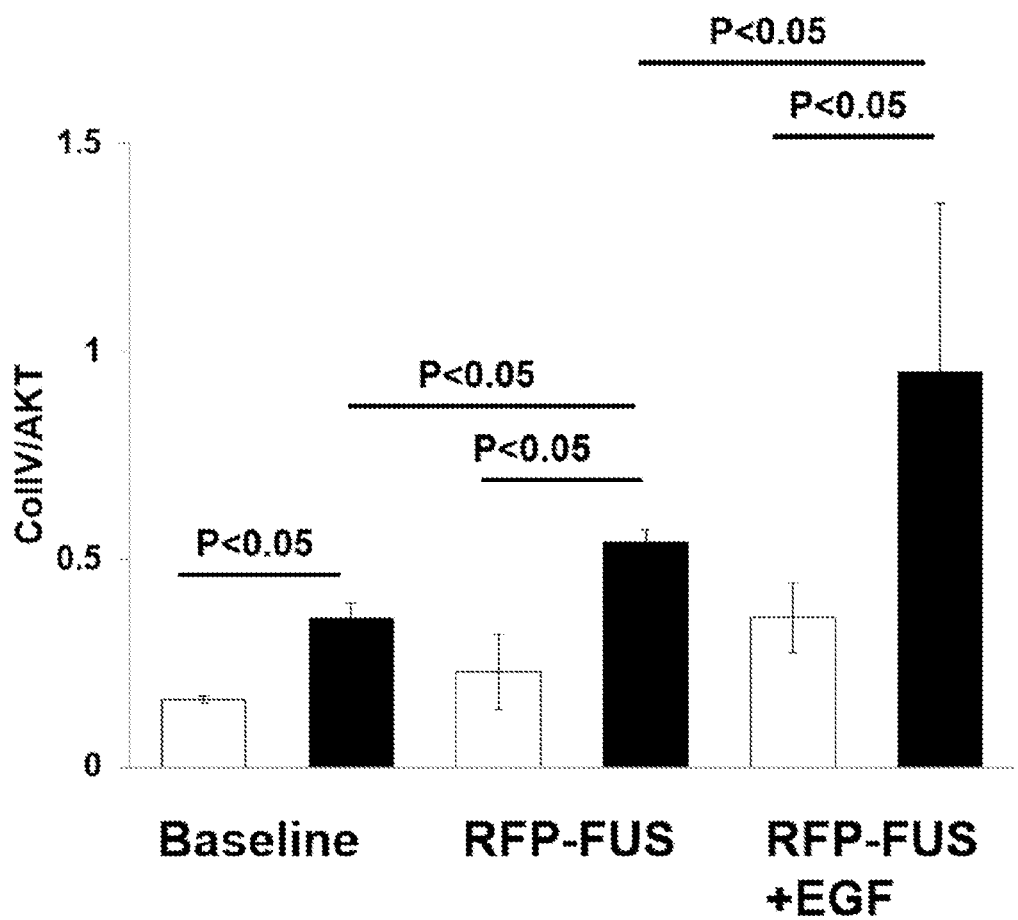

Mesangial cells were transiently transfected with murine FUS cDNA inserted downstream the Red Fluorescent Protein gene (RFP-FUS) (FIG. 6C) and its basal nuclear localization was determined. RFP-FUS was detected in the nuclei of both WT and Itgα1KO cells, although it was significantly more in the latter group (FIG. 6D,E). When cells were treated for 30 minutes with EGF, increased activation of EGFR was observed in both WT and Itgα1KO cells, although it was more evident in the Itgα1KO cells (FIG. 6A,B). Treatment with EGF, also significantly promoted more RFP-FUS nuclear translocation in Itgα1KO cells compared to WT cells (FIG. 6D,E).

Downregulation of FUS Decreased Basal Collagen Production in Itgα1KO Cells.

Figure 7A:
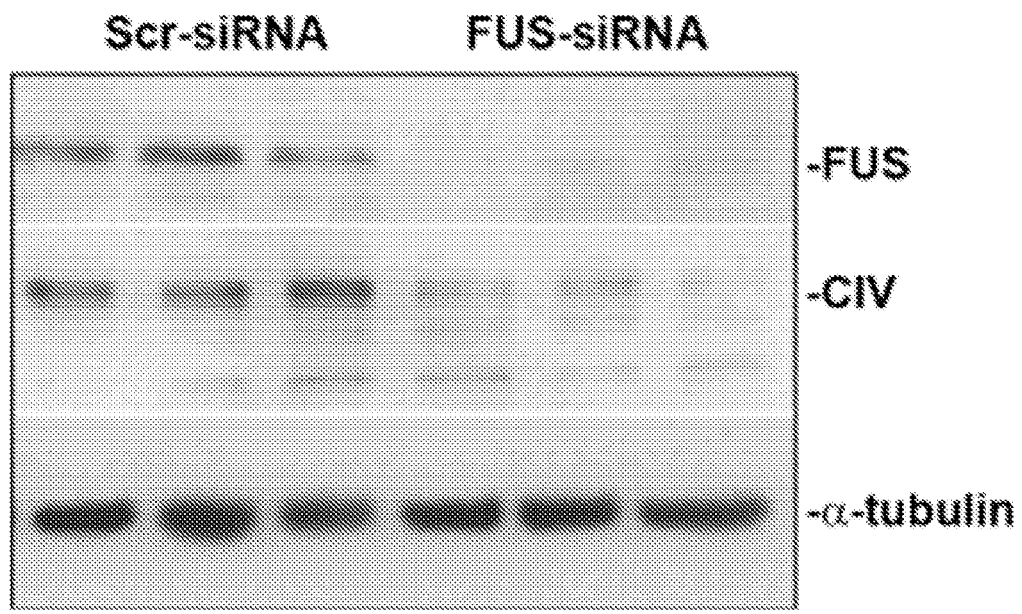
FIGS. 7A to 7C. (A, B) Itgα1KO mesangial cells were treated with scrambled-(Ser) or FUS-siRNA. 48 hours later the levels of FUS and collagen IV were analyzed by WB and quantified by densitometry analysis. (B, mean±SEM of 3 samples). (C) Itgα1KO cells were treated with Scr- or FUS-siRNA. 24 hours later they were transiently transfected with the collagen IV enhancer (E)/firefly luciferase or enhancer/promoter (E/P)/firefly luciferase constructs together with *renilla* luciferase cDNAs. 24 hours later, the levels of firefly/*renilla* luciferase activity were analyzed (mean±SEM of 4 samples).
Figure 7B:
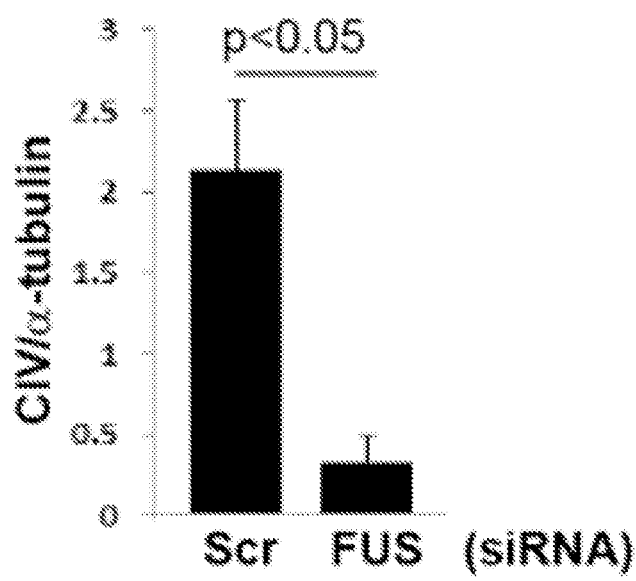

To determine whether the increased total and phosphorylated levels of nuclear FUS observed in Itgα1KO cells (FIGS. 4,5) are responsible for increased levels of collagen production in these cells (FIG. 5D,E), Itgα1KO cells were treated with either scrambled (Scr) or FUS siRNA and then the levels of FUS and collagen IV were analyzed. The focus was on collagen IV, as it is the major Itgα1β1 binding collagen (Gardner, H., et al. 1996. Dev Biol 175:301-313); and the collagen IV promoter and enhancer region contain several FUS responsive elements. FUS-siRNA, but not Scr-siRNA, significantly downregulated FUS levels and this event was accompanied by a significant decrease in collagen IV production (FIG. 7A,B). Thus, FUS either directly and/or indirectly controls collagen levels.

FUS Knockdown Decreases Collagen Transcription Levels.

Figure 7C:
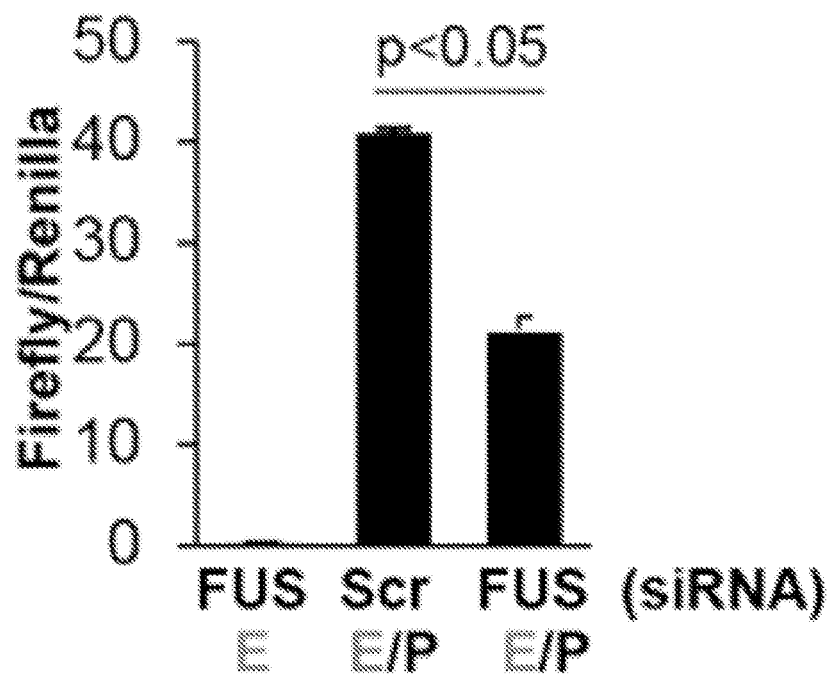

As the collagen IV enhancer/promoter contains FUS responsive elements, whether FUS can control collagen at the transcriptional levels was analyzed. Itgα1KO cells were treated with Scr- or FUS-siRNA and then the cells were transfected with a firefly luciferase reporter gene under the control of the collagen IV enhancer or enhancer/promoter. Analysis of luciferase activity (normalized to *renilla*) in cells treated with Scr-siRNA revealed the collagen IV enhancer by itself failed to promote luciferase transcription, while the collagen IV enhancer/promoter promoted robust luciferase transcription (FIG. 7C). Downregulation of FUS resulted in ~50% reduction in the collagen IV enhancer/activity, suggesting that FUS can control collagen IV production the transcriptional level (FIG. 7C).

Design and Testing of Cell-Penetrating Peptides that Inhibit FUS Nuclear Translocation.

At present there are no inhibitors available to prevent FUS function and/or nuclear translocation. FUS has an uncommon nuclear localization sequence (NLS) motif called PY-NLS because the PY is localized at the C-terminus of the protein (RGGRGGGDRGGFGPGKMDSRGEHRQDR-RERPY, SEQ ID NO:7). This non-classical NLS motif is recognized by transportin and methylation of the arginine in the RGG motif or phosphorylation of the tyrosine in the PY motif alters FUS/transportin interaction and interferes with FUS nuclear translocation (Zhang, Z. C., et al. 2012. Proc Natl Acad Sci USA 109:12017-12021).

Based on this finding, a peptide AAVALLPAVLLAL-LAPSRGEHRQDRRERPY (SEQ ID NO:8) was designed carrying a FUS PY-NLS derived peptide (bold) fused with the signal sequence hydrophobic region of FGF4 (Italicized). Signal sequence hydrophobic region was designed as a membrane translocating fragment that enables NLS to cross cell membrane bypassing endosomal pathway (Veach, R. A., et al. 2004. J Biol Chem 279:11425-11431). The mutated version of the fragment-designed peptide AAVALL- PAVLLALLAPSEGEHRADEEERGA (SEQ ID NO:13) contained amino acid replacements in PY-NLS of FUS.

Figure 8A:
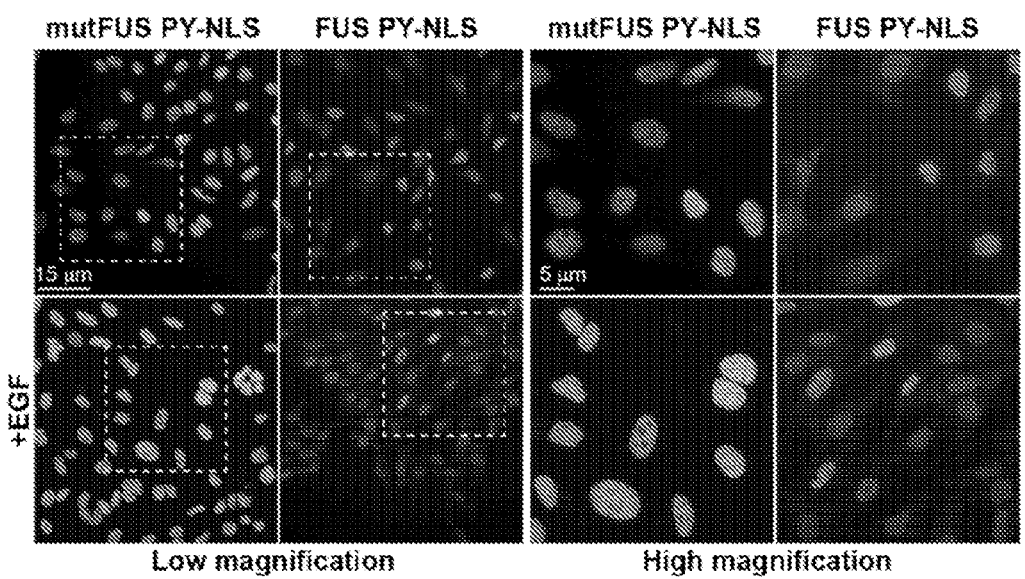
FIGS. 8A to 8D. (A) Itgα1KO mesangial cells were treated with 0.1 µM FUS PY-NLS derived peptide or its mutant form for 24 hours and then left untreated or treated with EGF (20 ng/ml) for 3 hours. Cells where stained with anti-FUS antibody (Red) or DAPI (Blue) to visualize FUS localization. (B) The intensity of FUS nuclear staining was measured using Image-J and expressed as mean of intensity/cell (mean±SEM of 50 cells). WT and Itgα1KO mesangial cells were treated with EGF for 0 or 24 hours in the presence of either FUS PY-NLS derived peptide or its mutant form for 24 hours. The levels of Collagen IV and FAK (as loading control) were then analyzed by Western blot (C) and quantified by densitometry analysis (D, mean±SEM of 3 samples).
Figure 8B:
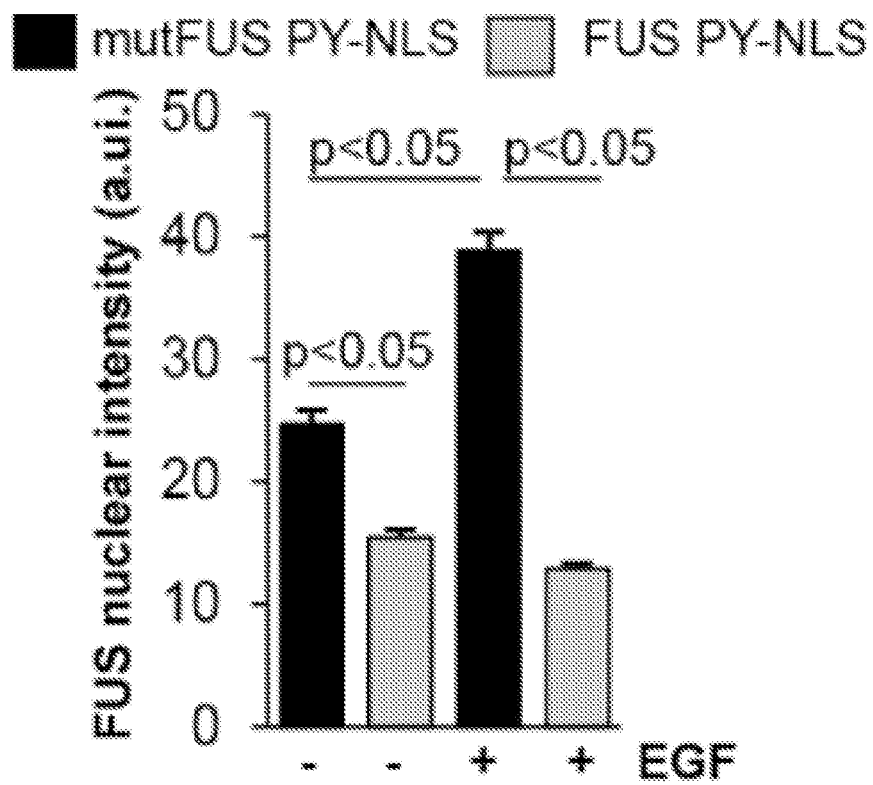
Figure 8C:
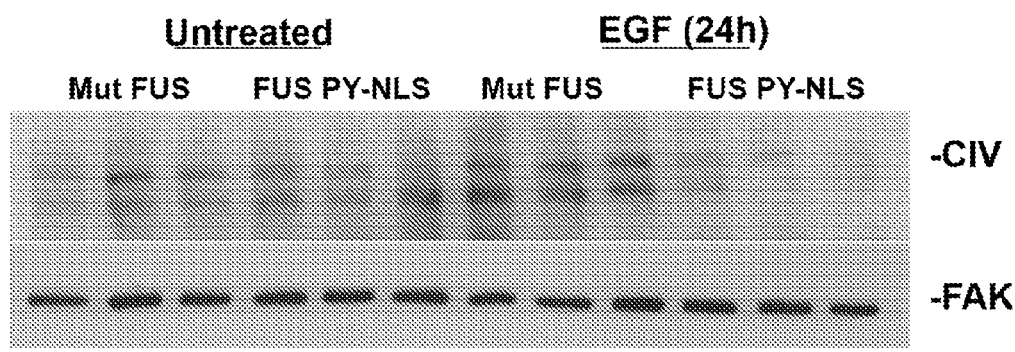
Figure 8D:
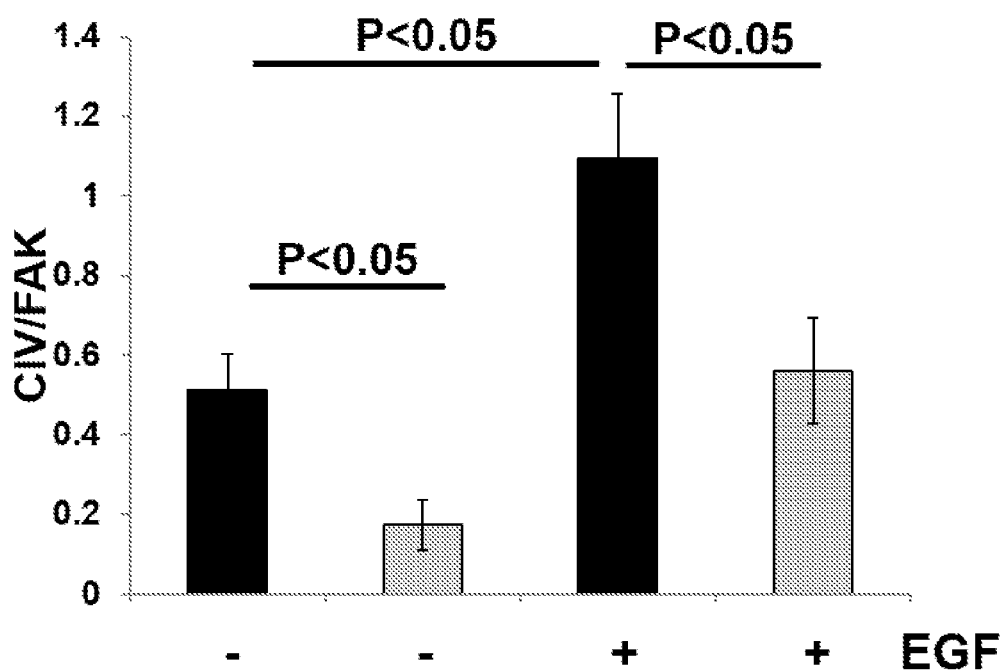
Figure 9A:
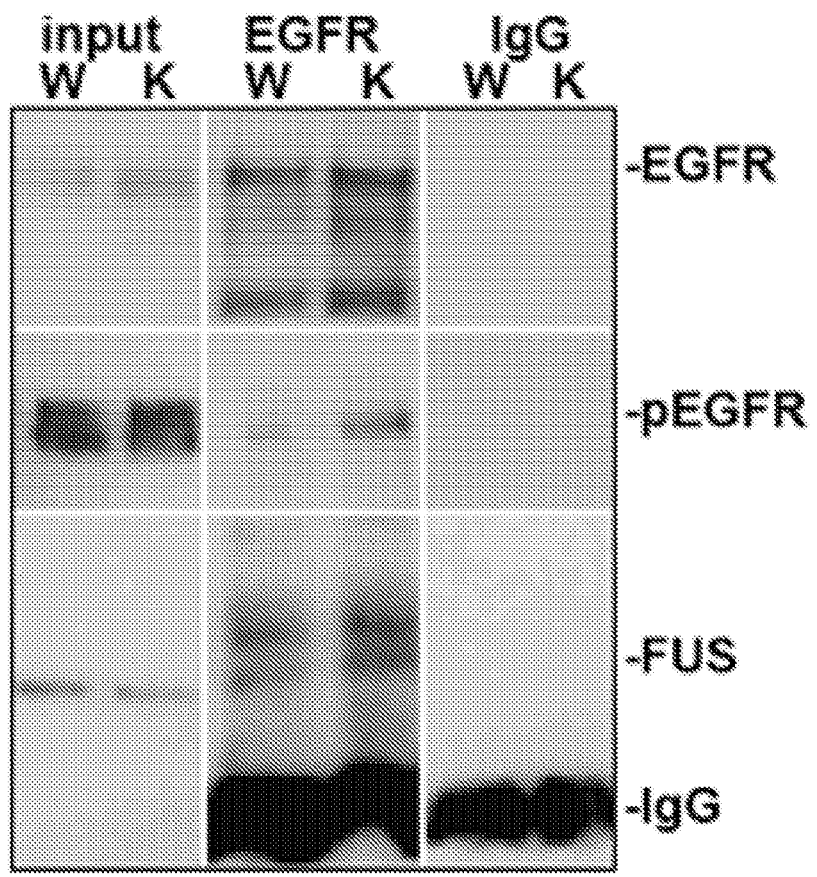
FIGS. 9A to 9C. (A) Lysates from WT (W) and Itgα1KO (K) mesangial cells were immuno-precipitated with anti-EGFR antibody or IgG and then analyzed by Western blot for levels of EGFR, phospho EGFR and FUS. (B, C) The levels of phosphor EGFR, EGFR and FUS were analyzed by densitometry and expressed as pEGFR/EGFR and FUS/EGFR ratio (n=4 experiments).
Figure 9B:
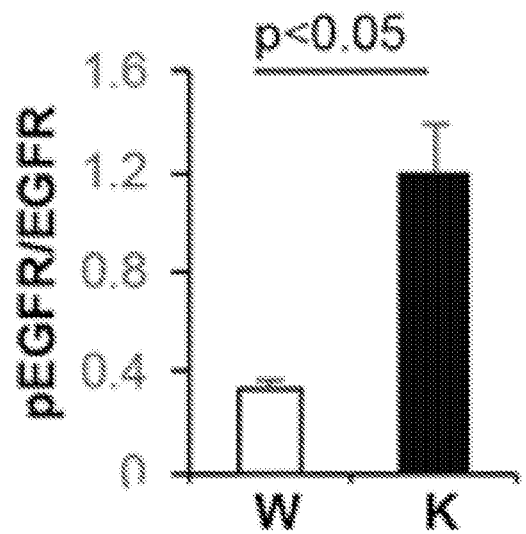
Figure 9C:
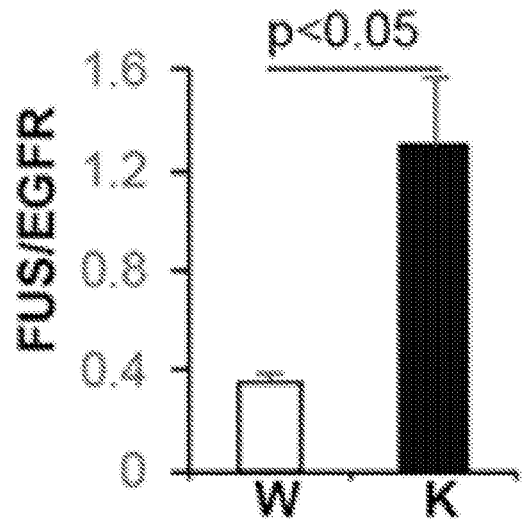

Both peptides were purified and tested for cytotoxicity at the concentrations used in these experiments. Itgα1KO mesangial cells were pre-treated with these peptides (0.1 µM) for 24 hours and then left untreated or treated with EGF for 3 hours. FUS localization was then analyzed by immunofluorescence using anti-FUS antibody. FUS PY-NSL derived peptide, but not its mutated version, significantly inhibited both basal and EGF-mediated FUS nuclear translocation (FIG. 8A, B). Cells treated with the FUS PY-NSL derived peptide also showed cytoplasmic FUS indicating that the peptide efficiently prevents FUS nuclear translocation (FIG. 8A).

Figure 10A:
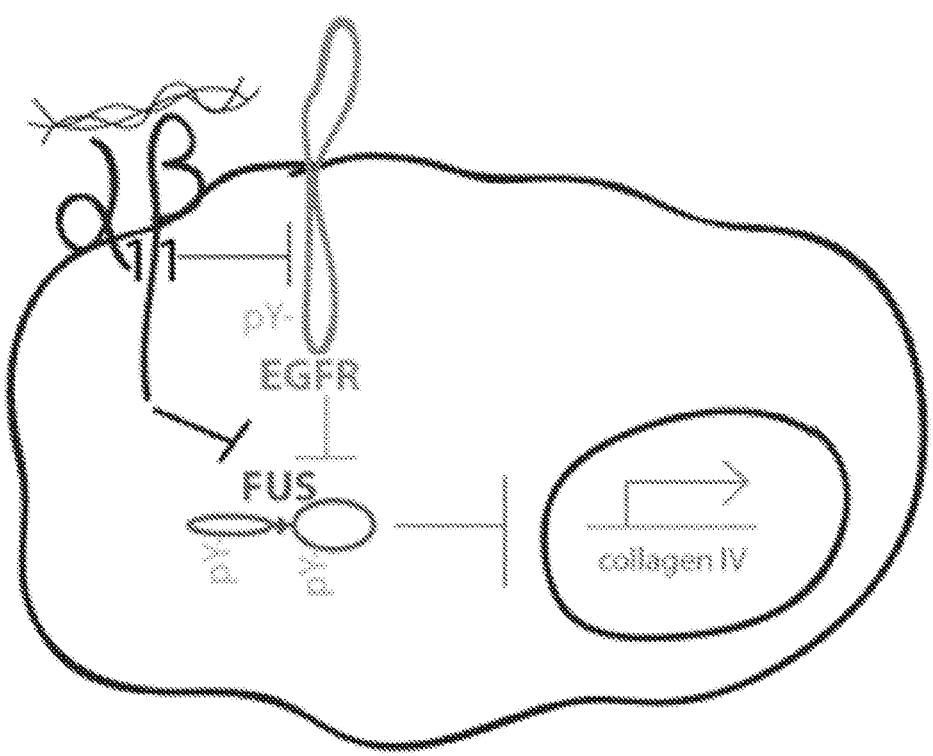
FIGS. 10A and 10B. Schematic representation of a possible Itgα1β1/FUS interaction in healthy WT (A) or Itgα1KO (B) mesangial cells. It was hypothesize that in healthy cells (A), Itgα1β1 prevents FUS tyrosine phosphorylation, nuclear translocation, and activation of collagen IV synthesis in a both EGFR-dependent and -independent manner. In Itgα1KO cells (B), increased phosphorylation of FUS leads to its association with transportin and nuclear translocation with consequent increased collagen IV synthesis.
Figure 10B:
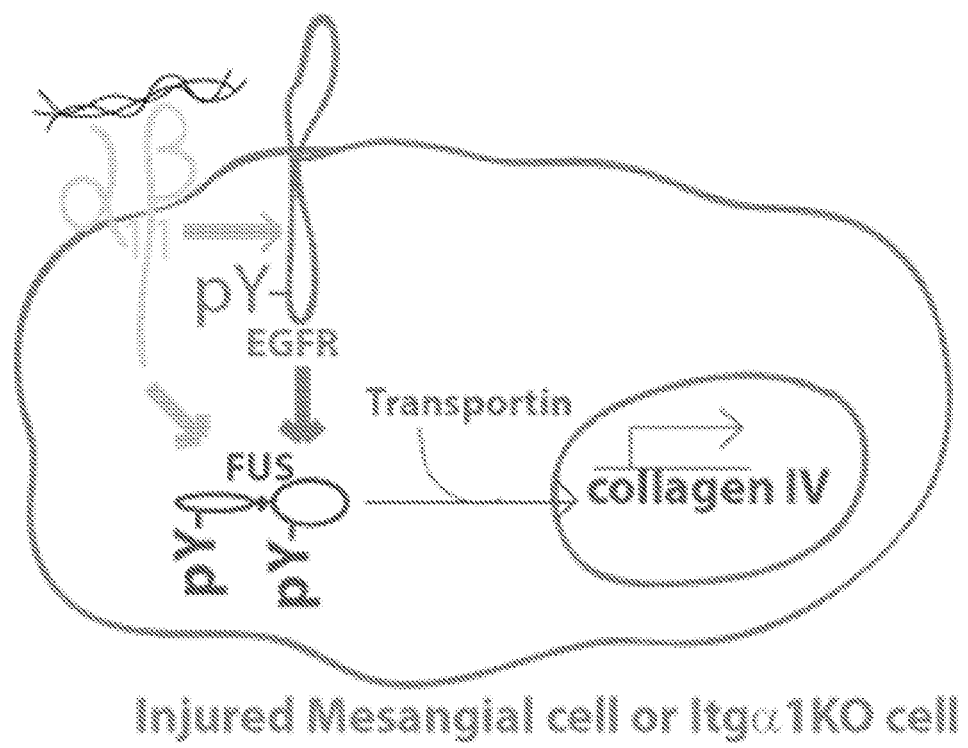
Figure 11:
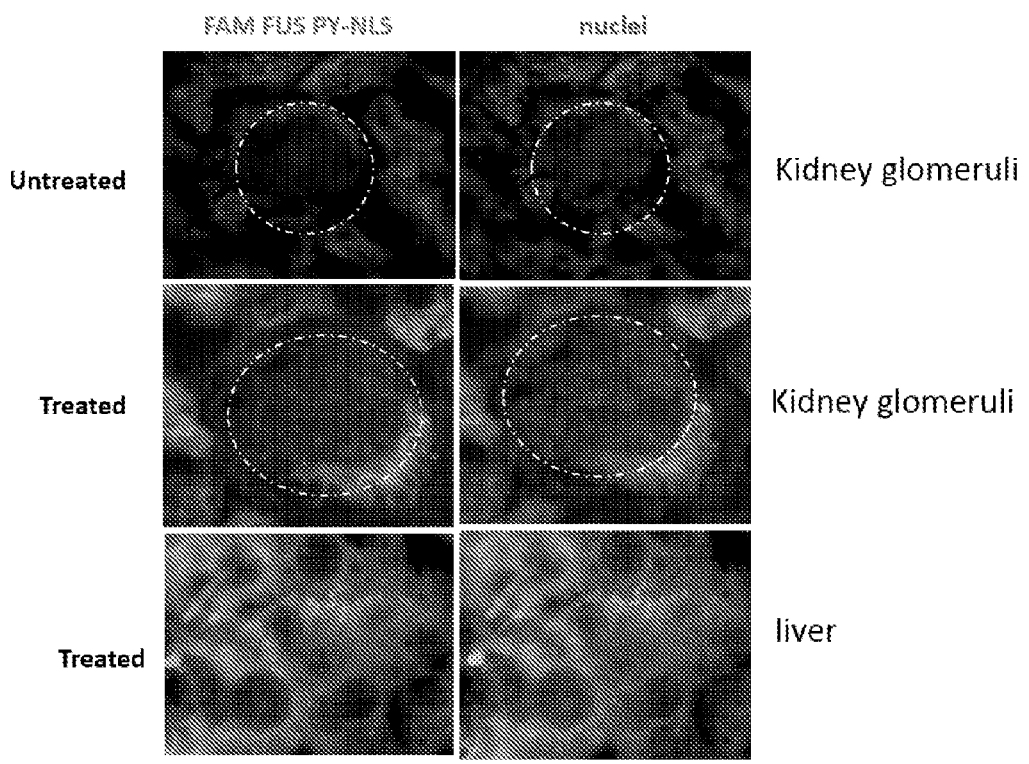
FIG. 11. In vivo delivery of FAM FUS-PY-NLS peptide injected 5 times every 2 hours. Mice were then sacrificed and kidney and liver frozen sections were analyzed under an epifluorescence microscope. Fluorescent peptide is displayed intracellularly in kidney glomeruli and liver cells.

Based on the finding that cells lacking Itgα1β1 show increased tyrosine phosphorylated and nuclear levels of FUS and that FUS nuclear levels are positively associated to collagen production, it is proposed that, in the course of glomerular injury, Itgα1β1 attenuates excessive and unwanted collagen synthesis by negatively regulating FUS tyrosine phosphorylation, nuclear translocation, and activation of collagen transcription (FIGS. 10A and 10B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated peptide comprising a transportin-binding moiety linked to a membrane translocating motif in a N- to C-terminal direction with the transportin-binding moiety at the N-terminal end, wherein the transportin-binding moiety inhibits Fused in Sarcoma (FUS) ribonucleoprotein from binding transportin; wherein the membrane translocating motif comprises the amino acid sequence AAVALLPAVL-LAVLAP (SEQ ID NO:5); and wherein the transportin-binding moiety comprises a C-terminal fragment of a FUS ribonucleoprotein comprising the amino acid sequence SRGEHRQDRRERPY (SEQ ID NO:1).

2. The isolated peptide of claim 1, wherein the peptide comprises the amino acid sequence as set forth in SEQ ID NO: 9.

3. The peptide of claim 1, wherein the peptide further comprises a glycine and/or serine linker joining the membrane translocating motif to the transportin-binding moiety; wherein the linker is a polyglycine linker, a polyserine linker, or a linker having a combination of glycine and serine, including repeating combinations.

4. An agent comprising the peptide of claim 1 fused to an organ-specific or cell-specific homing peptide as set forth in SEQ ID NO: 12, SEQ ID NO: 13, SEQ ID NO: 14, or SEQ ID NO: 15; or Fab antibody fragment recognizing an organ- or cell-specific epitope.

* * * * *

UNITED STATES PATENT AND TRADEMARK OFFICE
CERTIFICATE OF CORRECTION

PATENT NO. : 12,060,396 B2  
APPLICATION NO. : 16/481128  
DATED : August 13, 2024  
INVENTOR(S) : Ambra A. Pozzi Page 1 of 1

It is certified that error appears in the above-identified patent and that said Letters Patent is hereby corrected as shown below:

On the Title Page

Item [60]:
"Continuation of application No. 15/297,996, filed on Oct. 19, 2016, now Pat. No. 10,568,928..."
Should read:
--Continuation in part of application No. 15/297,996, filed on Oct. 19, 2016, now Pat. No. 10,568,928...--

Signed and Sealed this  
Fifth Day of November, 2024

Katherine Kelly Vidal  
*Director of the United States Patent and Trademark Office*

SEQUENCE LISTING

```
<160> NUMBER OF SEQ ID NOS: 15

<210> SEQ ID NO 1
<211> LENGTH: 14
<212> TYPE: PRT
<213> ORGANISM: Artificial Sequence
<220> FEATURE:
<223> OTHER INFORMATION: synthetic construct

<400> SEQUENCE: 1

Ser Arg Gly Glu His Arg Gln Asp Arg Arg Glu Arg Pro Tyr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(4)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid

<400> SEQUENCE: 2

Xaa Xaa Xaa Xaa Leu Leu Pro Xaa Xaa Leu Leu Ala Leu Leu Ala Pro
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(4)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid

<400> SEQUENCE: 3

Xaa Xaa Xaa Xaa Leu Leu Pro Xaa Xaa Leu Leu Ala Val Leu Ala Pro
1               5                   10                  15
```

```
<210> SEQ ID NO 4
<211> LENGTH: 16
<212> TYPE: PRT
<213> ORGANISM: Artificial Sequence
<220> FEATURE:
<223> OTHER INFORMATION: synthetic construct

<400> SEQUENCE: 4

Ala Ala Val Ala Leu Leu Pro Ala Val Leu Leu Ala Leu Leu Ala Pro
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetic construct

<400> SEQUENCE: 5

Ala Ala Val Ala Leu Leu Pro Ala Val Leu Leu Ala Val Leu Ala Pro
1               5                   10                  15

<210> SEQ ID NO 6
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is 1 to 10 independently selected amino
      acids
<220> FEATURE:
<221> NAME/KEY: MISC_FEATURE
<222> LOCATION: (5)..(5)
<223> OTHER INFORMATION: Xaa is 1 to 10 independently selected amino
      acids

<400> SEQUENCE: 6

Xaa Gly Phe Glu Xaa
1               5

<210> SEQ ID NO 7
<211> LENGTH: 32
<212> TYPE: PRT
<213> ORGANISM: Artificial Sequence
<220> FEATURE:
<223> OTHER INFORMATION: synthetic construct

<400> SEQUENCE: 7

Arg Gly Gly Arg Gly Gly Gly Asp Arg Gly Phe Gly Pro Gly Lys
1               5                   10                  15

Met Asp Ser Arg Gly Glu His Arg Gln Asp Arg Gly Glu Arg Pro Tyr
                20                  25                  30

<210> SEQ ID NO 8
<211> LENGTH: 30
<212> TYPE: PRT
<213> ORGANISM: Artificial Sequence
<220> FEATURE:
<223> OTHER INFORMATION: synthetic construct

<400> SEQUENCE: 8

Ala Ala Val Ala Leu Leu Pro Ala Val Leu Leu Ala Leu Leu Ala Pro
1               5                   10                  15

Ser Arg Gly Glu His Arg Gln Asp Arg Arg Glu Arg Pro Tyr
```

```
                    20                  25                  30

<210> SEQ ID NO 9
<211> LENGTH: 30
<212> TYPE: PRT
<213> ORGANISM: Artificial Sequence
<220> FEATURE:
<223> OTHER INFORMATION: synthetic construct

<400> SEQUENCE: 9

Ala Ala Val Ala Leu Leu Pro Ala Val Leu Leu Ala Val Leu Ala Pro
1               5                   10                  15

Ser Arg Gly Glu His Arg Gln Asp Arg Arg Glu Arg Pro Tyr
            20                  25                  30

<210> SEQ ID NO 10
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(4)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa can be a valine or leucine

<400> SEQUENCE: 10

Xaa Xaa Xaa Xaa Leu Leu Pro Xaa Xaa Leu Leu Ala Xaa Leu Ala Pro
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (13)..(13)
<223> OTHER INFORMATION: Xaa can be a valine or leucine

<400> SEQUENCE: 11

Ala Ala Val Ala Leu Leu Pro Ala Val Leu Leu Ala Xaa Leu Ala Pro
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: synthetic construct

<400> SEQUENCE: 12

Cys Ala Arg Ser Lys Asn Lys Asp Cys
1               5

<210> SEQ ID NO 13
<211> LENGTH: 30
<212> TYPE: PRT
<213> ORGANISM: Artificial Sequence
<220> FEATURE:
```

```
<223> OTHER INFORMATION: synthetic construct

<400> SEQUENCE: 13

Ala Ala Val Ala Leu Leu Pro Ala Val Leu Leu Ala Leu Leu Ala Pro
1               5                   10                  15

Ser Glu Gly Glu His Arg Ala Asp Glu Glu Arg Gly Ala
            20                  25              30

<210> SEQ ID NO 14
<211> LENGTH: 13
<212> TYPE: PRT
<213> ORGANISM: Artificial Sequence
<220> FEATURE:
<223> OTHER INFORMATION: synthetic construct

<400> SEQUENCE: 14

Cys Gly Phe Glu Cys Val Arg Gln Cys Pro Glu Arg Cys
1               5                   10

<210> SEQ ID NO 15
<211> LENGTH: 8
<212> TYPE: PRT
<213> ORGANISM: Artificial Sequence
<220> FEATURE:
<223> OTHER INFORMATION: synthetic construct

<400> SEQUENCE: 15

Cys Gly Phe Glu Leu Glu Thr Cys
1               5
```